United States Patent
Echauz et al.

(10) Patent No.: US 8,786,624 B2
(45) Date of Patent: Jul. 22, 2014

(54) PROCESSING FOR MULTI-CHANNEL SIGNALS

(75) Inventors: Javier Ramón Echauz, Alpharetta, GA (US); David E. Snyder, Bainbridge Island, WA (US); Kent W. Leyde, Sammamish, WA (US)

(73) Assignee: Cyberonics, Inc., Houston, TX (US)

(*) Notice: Subject to any disclaimer, the term of this patent is extended or adjusted under 35 U.S.C. 154(b) by 856 days.

(21) Appl. No.: 12/792,582

(22) Filed: Jun. 2, 2010

(65) Prior Publication Data

US 2010/0302270 A1    Dec. 2, 2010

Related U.S. Application Data

(60) Provisional application No. 61/183,449, filed on Jun. 2, 2009.

(51) Int. Cl.
| | |
|---|---|
| G06T 11/20 | (2006.01) |
| G09G 5/02 | (2006.01) |
| G06F 19/00 | (2011.01) |
| G06F 17/18 | (2006.01) |

(52) U.S. Cl.
USPC .............. 345/589; 345/440; 702/66; 702/180

(58) Field of Classification Search
None
See application file for complete search history.

(56) References Cited

U.S. PATENT DOCUMENTS

| | | | |
|---|---|---|---|
| 3,218,638 A | 11/1965 | Honig | |
| 3,498,287 A | 3/1970 | Ertl | |
| 3,522,811 A | 8/1970 | Schwartz | |
| 3,575,162 A | 4/1971 | Gaarder | |
| 3,837,331 A | 9/1974 | Ross | |
| 3,850,161 A | 11/1974 | Liss | |
| 3,863,625 A | 2/1975 | Viglione et al. | |
| 3,882,850 A | 5/1975 | Bailin et al. | |
| 3,918,461 A | 11/1975 | Cooper | |
| 3,967,616 A | 7/1976 | Ross | |

(Continued)

FOREIGN PATENT DOCUMENTS

| | | |
|---|---|---|
| CA | 2251852 | 4/1999 |
| CA | 2423840 | 2/2002 |

(Continued)

OTHER PUBLICATIONS

Spector et al.; High and Low Perceived Self-Control of Epileptic Seizures; Epilepsia, vol. 42(4), Apr. 2001; pp. 556-564.

(Continued)

*Primary Examiner* — Kee M Tung
*Assistant Examiner* — Michelle Chin
(74) *Attorney, Agent, or Firm* — Cyberonics, Inc.

(57) ABSTRACT

Method and apparatus for improved processing for multi-channel signals. In an exemplary embodiment, an anomaly metric is computed for a multi-channel signal over a time window. The magnitude of the anomaly metric may be used to determine whether an anomaly is present in the multi-channel signal over the time window. In an exemplary embodiment, the anomaly metric may be a condition number associated with the singular values of the multi-channel signal over the time window, as further adjusted by the number of channels to produce a data condition number. Applications of the anomaly metric computation include the scrubbing of signal archives for epileptic seizure detection/prediction/counter-prediction algorithm training, pre-processing of multi-channel signals for real-time monitoring of bio-systems, and boot-up and/or adaptive self-checking of such systems during normal operation.

12 Claims, 15 Drawing Sheets

(56) References Cited

U.S. PATENT DOCUMENTS

| | | |
|---|---|---|
| 3,993,046 A | 11/1976 | Fernandez |
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,545,388 A | 10/1985 | John |
| 4,556,061 A | 12/1985 | Barreras et al. |
| 4,566,464 A | 1/1986 | Piccone et al. |
| 4,573,481 A | 3/1986 | Bullara |
| 4,579,125 A | 4/1986 | Strobl et al. |
| 4,590,946 A | 5/1986 | Loeb |
| 4,612,934 A | 9/1986 | Borkan |
| 4,679,144 A | 7/1987 | Cox et al. |
| 4,686,999 A | 8/1987 | Snyder et al. |
| 4,702,254 A | 10/1987 | Zabara |
| 4,735,208 A | 4/1988 | Wyler et al. |
| 4,768,176 A | 8/1988 | Kehr et al. |
| 4,768,177 A | 8/1988 | Kehr et al. |
| 4,785,827 A | 11/1988 | Fischer |
| 4,793,353 A | 12/1988 | Borkam |
| 4,817,628 A | 4/1989 | Zealear |
| 4,838,272 A | 6/1989 | Lieber |
| 4,844,075 A | 7/1989 | Liss et al. |
| 4,852,573 A | 8/1989 | Kennedy |
| 4,867,164 A | 9/1989 | Zabara |
| 4,873,981 A | 10/1989 | Abrams et al. |
| 4,878,498 A | 11/1989 | Abrams et al. |
| 4,903,702 A | 2/1990 | Putz |
| 4,920,979 A | 5/1990 | Bullara |
| 4,926,865 A | 5/1990 | Oman |
| 4,955,380 A | 9/1990 | Edell |
| 4,978,680 A | 12/1990 | Sofia |
| 4,979,511 A | 12/1990 | Terry |
| 4,991,582 A | 2/1991 | Byers et al. |
| 5,010,891 A | 4/1991 | Chamoun |
| 5,016,635 A | 5/1991 | Graupe |
| 5,025,807 A | 6/1991 | Zabara |
| 5,031,618 A | 7/1991 | Mullett |
| 5,070,873 A | 12/1991 | Graupe et al. |
| 5,082,861 A | 1/1992 | Sofia |
| 5,097,835 A | 3/1992 | Putz |
| RE34,015 E | 8/1992 | Duffy |
| 5,154,172 A | 10/1992 | Terry |
| 5,167,229 A | 12/1992 | Peckham et al. |
| 5,179,950 A | 1/1993 | Stanislaw |
| 5,181,520 A | 1/1993 | Wertheim et al. |
| 5,186,170 A | 2/1993 | Varichio |
| 5,188,104 A | 2/1993 | Wernicke |
| 5,190,029 A | 3/1993 | Byron et al. |
| 5,193,539 A | 3/1993 | Schulman et al. |
| 5,193,540 A | 3/1993 | Schulman et al. |
| 5,205,285 A | 4/1993 | Baker, Jr. |
| 5,215,086 A | 6/1993 | Terry, Jr. et al. |
| 5,215,088 A | 6/1993 | Normann |
| 5,215,089 A | 6/1993 | Baker, Jr. |
| 5,222,494 A | 6/1993 | Baker, Jr. |
| 5,222,503 A | 6/1993 | Ives |
| 5,231,988 A | 8/1993 | Wernicke et al. |
| 5,235,980 A | 8/1993 | Varichio et al. |
| 5,237,991 A | 8/1993 | Baker, Jr. |
| 5,251,634 A | 10/1993 | Weinberg |
| 5,263,480 A | 11/1993 | Wernicke et al. |
| 5,265,619 A | 11/1993 | Comby et al. |
| 5,269,302 A | 12/1993 | Swartz et al. |
| 5,269,303 A | 12/1993 | Wernicke et al. |
| 5,269,315 A | 12/1993 | Leuchter et al. |
| 5,292,772 A | 3/1994 | Sofia |
| 5,293,879 A | 3/1994 | Vonk |
| 5,299,118 A | 3/1994 | Martens et al. |
| 5,299,569 A | 4/1994 | Wernicke et al. |
| 5,300,094 A | 4/1994 | Kallok et al. |
| 5,304,206 A | 4/1994 | Baker, Jr. et al. |
| 5,311,876 A | 5/1994 | Olsen et al. |
| 5,312,439 A | 5/1994 | Loeb |
| 5,314,458 A | 5/1994 | Najafi et al. |
| 5,324,316 A | 6/1994 | Schulman et al. |
| 5,330,515 A | 7/1994 | Rutecki et al. |
| 5,335,657 A | 8/1994 | Terry et al. |
| 5,342,408 A | 8/1994 | deCoriolis et al. |
| 5,342,409 A | 8/1994 | Mullett |
| 5,343,064 A | 8/1994 | Spangler et al. |
| 5,349,962 A | 9/1994 | Lockard et al. |
| 5,351,394 A | 10/1994 | Weinberg |
| 5,361,760 A | 11/1994 | Normann |
| 5,365,939 A | 11/1994 | Ochs |
| 5,376,359 A | 12/1994 | Johnson |
| 5,392,788 A | 2/1995 | Hudspeth |
| 5,405,365 A | 4/1995 | Hoegnelid et al. |
| 5,405,367 A | 4/1995 | Schulman et al. |
| 5,411,540 A | 5/1995 | Edell et al. |
| 5,458,117 A | 10/1995 | Chamoun |
| 5,474,547 A | 12/1995 | Aebischer et al. |
| 5,476,494 A | 12/1995 | Edell et al. |
| 5,486,999 A | 1/1996 | Mebane |
| 5,513,649 A | 5/1996 | Gevins |
| 5,517,115 A * | 5/1996 | Prammer ................. 324/303 |
| 5,531,778 A | 7/1996 | Maschino et al. |
| 5,540,730 A | 7/1996 | Terry |
| 5,540,734 A | 7/1996 | Zabara |
| 5,549,656 A | 8/1996 | Reiss |
| 5,555,191 A | 9/1996 | Hripcsak |
| 5,571,148 A | 11/1996 | Loeb et al. |
| 5,571,150 A | 11/1996 | Wernicke |
| 5,575,813 A | 11/1996 | Edell et al. |
| 5,578,036 A | 11/1996 | Stone et al. |
| 5,611,350 A | 3/1997 | John |
| 5,626,145 A | 5/1997 | Clapp et al. |
| 5,626,627 A | 5/1997 | Krystal et al. |
| 5,638,826 A | 6/1997 | Wolpaw |
| 5,649,068 A | 7/1997 | Boser et al. |
| 5,672,154 A | 9/1997 | Sillen et al. |
| 5,683,422 A | 11/1997 | Rise |
| 5,683,432 A | 11/1997 | Goedeke et al. |
| 5,690,681 A | 11/1997 | Geddes et al. |
| 5,690,691 A | 11/1997 | Chen et al. |
| 5,697,369 A | 12/1997 | Long |
| 5,700,282 A | 12/1997 | Zabara |
| 5,704,352 A | 1/1998 | Tremblay et al. |
| 5,707,400 A | 1/1998 | Terry et al. |
| 5,711,316 A | 1/1998 | Elsberry et al. |
| 5,713,923 A | 2/1998 | Ward et al. |
| 5,715,821 A | 2/1998 | Faupel |
| 5,716,377 A | 2/1998 | Rise et al. |
| 5,720,294 A | 2/1998 | Skinner |
| 5,735,814 A | 4/1998 | Elsberry et al. |
| 5,743,860 A | 4/1998 | Hively et al. |
| 5,752,979 A | 5/1998 | Benabid |
| 5,769,778 A | 6/1998 | Abrams et al. |
| 5,776,434 A | 7/1998 | Purewal et al. |
| 5,782,798 A | 7/1998 | Rise |
| 5,782,874 A | 7/1998 | Loos |
| 5,792,186 A | 8/1998 | Rise |
| 5,800,474 A | 9/1998 | Benabid et al. |
| 5,813,993 A | 9/1998 | Kaplan |
| 5,814,014 A | 9/1998 | Elsberry et al. |
| 5,815,413 A | 9/1998 | Hively et al. |
| 5,816,247 A | 10/1998 | Maynard |
| 5,824,021 A | 10/1998 | Rise |
| 5,832,932 A | 11/1998 | Elsberry et al. |
| 5,833,709 A | 11/1998 | Rise et al. |
| 5,857,978 A | 1/1999 | Hively et al. |
| 5,862,803 A | 1/1999 | Besson et al. |
| 5,876,424 A | 3/1999 | O'Phelan et al. |
| 5,899,922 A | 5/1999 | Loos |
| 5,913,881 A | 6/1999 | Benz et al. |
| 5,916,239 A | 6/1999 | Geddes et al. |
| 5,917,429 A | 6/1999 | Otis, Jr. et al. |

(56) References Cited

U.S. PATENT DOCUMENTS

| | | |
|---|---|---|
| 5,928,272 A | 7/1999 | Adkins |
| 5,931,791 A | 8/1999 | Saltzstein et al. |
| 5,938,689 A | 8/1999 | Fischell et al. |
| 5,941,906 A | 8/1999 | Barreras et al. |
| 5,950,632 A | 9/1999 | Reber et al. |
| 5,957,861 A | 9/1999 | Combs et al. |
| 5,971,594 A | 10/1999 | Sahai et al. |
| 5,975,085 A | 11/1999 | Rise |
| 5,978,702 A | 11/1999 | Ward et al. |
| 5,978,710 A | 11/1999 | Prutchi et al. |
| 5,995,868 A | 11/1999 | Dorfmeister et al. |
| 6,006,124 A | 12/1999 | Fischell et al. |
| 6,016,449 A | 1/2000 | Fischell et al. |
| 6,018,682 A | 1/2000 | Rise |
| 6,042,548 A | 3/2000 | Giuffre |
| 6,042,579 A | 3/2000 | Elsberry et al. |
| 6,051,017 A | 4/2000 | Loeb et al. |
| 6,052,619 A | 4/2000 | John |
| 6,061,593 A | 5/2000 | Fischell et al. |
| 6,066,163 A | 5/2000 | John |
| 6,081,744 A | 6/2000 | Loos |
| 6,094,598 A | 7/2000 | Elsberry et al. |
| 6,109,269 A | 8/2000 | Rise et al. |
| 6,117,066 A | 9/2000 | Abrams et al. |
| 6,128,537 A | 10/2000 | Rise et al. |
| 6,128,538 A | 10/2000 | Fischell et al. |
| 6,134,474 A | 10/2000 | Fischell et al. |
| 6,161,045 A | 12/2000 | Fischell et al. |
| 6,167,304 A | 12/2000 | Loos |
| 6,171,239 B1 | 1/2001 | Humphrey |
| 6,176,242 B1 | 1/2001 | Rise |
| 6,205,359 B1 | 3/2001 | Boveja |
| 6,208,893 B1 | 3/2001 | Hofmann |
| 6,221,011 B1 | 4/2001 | Bardy |
| 6,227,203 B1 | 5/2001 | Rise et al. |
| 6,230,049 B1 | 5/2001 | Fischell et al. |
| 6,248,126 B1 | 6/2001 | Lesser et al. |
| 6,249,703 B1 | 6/2001 | Stanton |
| 6,263,237 B1 | 7/2001 | Rise |
| 6,280,198 B1 | 8/2001 | Calhoun et al. |
| 6,304,775 B1 | 10/2001 | Iasemidis et al. |
| 6,309,406 B1 | 10/2001 | Jones et al. |
| 6,328,699 B1 | 12/2001 | Eigler |
| 6,337,997 B1 | 1/2002 | Rise |
| 6,339,725 B1 | 1/2002 | Naritoku |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,356,788 B2 | 3/2002 | Boveja |
| 6,358,203 B2 | 3/2002 | Bardy |
| 6,358,281 B1 | 3/2002 | Berrang et al. |
| 6,360,122 B1 | 3/2002 | Fischell |
| 6,366,813 B1 | 4/2002 | DiLorenzo |
| 6,366,814 B1 | 4/2002 | Boveja |
| 6,374,140 B1 | 4/2002 | Rise |
| 6,386,882 B1 | 5/2002 | Linberg |
| 6,402,678 B1 | 6/2002 | Fischell et al. |
| 6,411,854 B1 | 6/2002 | Tziviskos et al. |
| 6,427,086 B1 | 7/2002 | Fischell et al. |
| 6,434,419 B1 | 8/2002 | Gevins et al. |
| 6,442,421 B1 | 8/2002 | Le Van Quyen et al. |
| 6,443,891 B1 | 9/2002 | Grevious |
| 6,453,198 B1 | 9/2002 | Torgerson |
| 6,463,328 B1 | 10/2002 | John |
| 6,466,822 B1 | 10/2002 | Pless |
| 6,471,645 B1 | 10/2002 | Warkentin et al. |
| 6,473,639 B1 | 10/2002 | Fischell et al. |
| 6,473,644 B1 | 10/2002 | Terry et al. |
| 6,480,743 B1 | 11/2002 | Kirkpatrick |
| 6,484,132 B1 | 11/2002 | Hively et al. |
| 6,488,617 B1 | 12/2002 | Katz |
| 6,496,724 B1 | 12/2002 | Levendowski et al. |
| 6,505,077 B1 | 1/2003 | Kast et al. |
| 6,510,340 B1 | 1/2003 | Jordan |
| 6,511,424 B1 | 1/2003 | Moore-Ede |
| 6,529,774 B1 | 3/2003 | Greene |
| 6,534,693 B2 | 3/2003 | Fischell et al. |
| 6,547,746 B1 | 4/2003 | Marino |
| 6,549,804 B1 | 4/2003 | Osorio et al. |
| 6,553,262 B1 | 4/2003 | Lang et al. |
| 6,560,486 B1 | 5/2003 | Osorio et al. |
| 6,571,123 B2 | 5/2003 | Ives et al. |
| 6,571,125 B2 | 5/2003 | Thompson |
| 6,572,528 B2 | 6/2003 | Rohan et al. |
| 6,587,719 B1 | 7/2003 | Barrett et al. |
| 6,591,132 B2 | 7/2003 | Gotman et al. |
| 6,591,137 B1 | 7/2003 | Fischell et al. |
| 6,591,138 B1 | 7/2003 | Fischell et al. |
| 6,597,954 B1 | 7/2003 | Pless et al. |
| 6,600,956 B2 | 7/2003 | Maschino |
| 6,609,025 B2 | 8/2003 | Barrett et al. |
| 6,618,623 B1 | 9/2003 | Pless et al. |
| 6,620,415 B2 | 9/2003 | Donovan |
| 6,622,036 B1 | 9/2003 | Suffin |
| 6,622,038 B2 | 9/2003 | Barrett et al. |
| 6,622,041 B2 | 9/2003 | Terry et al. |
| 6,622,047 B2 | 9/2003 | Barrett et al. |
| 6,658,287 B1 | 12/2003 | Litt et al. |
| 6,665,562 B2 | 12/2003 | Gluckman et al. |
| 6,668,191 B1 | 12/2003 | Boveja |
| 6,671,555 B2 | 12/2003 | Gielen |
| 6,678,548 B1 | 1/2004 | Echauz et al. |
| 6,684,105 B2 | 1/2004 | Cohen et al. |
| 6,687,538 B1 | 2/2004 | Hrdlicka et al. |
| 6,735,467 B2 | 5/2004 | Wilson |
| 6,760,626 B1 | 7/2004 | Boveja |
| 6,768,969 B1 | 7/2004 | Nikitin et al. |
| 6,778,854 B2 | 8/2004 | Puskas |
| 6,782,292 B2 | 8/2004 | Whitehurst |
| 6,819,956 B2 | 11/2004 | DiLorenzo |
| 6,879,859 B1 | 4/2005 | Boveja |
| 6,893,395 B1 | 5/2005 | Kraus et al. |
| 6,901,294 B1 | 5/2005 | Whitehurst et al. |
| 6,901,296 B1 | 5/2005 | Whitehurst et al. |
| 6,912,419 B2 | 6/2005 | Hill |
| 6,921,538 B2 | 7/2005 | Donovan |
| 6,921,541 B2 | 7/2005 | Chasin et al. |
| 6,923,784 B2 | 8/2005 | Stein |
| 6,931,274 B2 | 8/2005 | Williams |
| 6,934,580 B1 | 8/2005 | Osorio |
| 6,937,891 B2 | 8/2005 | Leinders et al. |
| 6,944,501 B1 | 9/2005 | Pless |
| 6,950,706 B2 | 9/2005 | Rodriguez |
| 6,973,342 B1 | 12/2005 | Swanson |
| 6,990,372 B2 | 1/2006 | Perron et al. |
| 7,010,351 B2 | 3/2006 | Firlik et al. |
| 7,089,059 B1 | 8/2006 | Pless |
| 7,174,212 B1 | 2/2007 | Klehn et al. |
| 7,177,701 B1 | 2/2007 | Pianca |
| 7,185,283 B1 * | 2/2007 | Takahashi ............ 715/723 |
| 7,209,787 B2 | 4/2007 | DiLorenzo |
| 7,212,851 B2 | 5/2007 | Donoghue et al. |
| 7,231,254 B2 | 6/2007 | DiLorenzo |
| 7,242,984 B2 | 7/2007 | DiLorenzo |
| 7,277,758 B2 | 10/2007 | DiLorenzo |
| 7,324,851 B1 | 1/2008 | DiLorenzo |
| 7,373,198 B2 | 5/2008 | Bibian et al. |
| 7,403,820 B2 | 7/2008 | DiLorenzo |
| 7,463,917 B2 | 12/2008 | Martinez |
| 7,623,928 B2 | 11/2009 | DiLorenzo |
| 7,631,015 B2 | 12/2009 | Gupta et al. |
| 7,747,325 B2 | 6/2010 | DiLorenzo |
| 7,805,196 B2 | 9/2010 | Miesel et al. |
| 7,853,329 B2 | 12/2010 | DiLorenzo |
| 7,881,798 B2 | 2/2011 | Miesel et al. |
| 8,036,736 B2 | 10/2011 | Snyder et al. |
| 8,055,348 B2 | 11/2011 | Heruth et al. |
| 8,125,484 B2 * | 2/2012 | Gering ............ 345/440 |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0035338 A1 | 3/2002 | Dear et al. |

(56) References Cited

U.S. PATENT DOCUMENTS

| | | |
|---|---|---|
| 2002/0054694 A1 | 5/2002 | Vachtsevanos et al. |
| 2002/0072770 A1 | 6/2002 | Pless |
| 2002/0072776 A1 | 6/2002 | Osorio et al. |
| 2002/0072782 A1 | 6/2002 | Osorio et al. |
| 2002/0077670 A1 | 6/2002 | Archer et al. |
| 2002/0095099 A1 | 7/2002 | Quyen et al. |
| 2002/0099412 A1 | 7/2002 | Fischell et al. |
| 2002/0103512 A1 | 8/2002 | Echauz et al. |
| 2002/0109621 A1 | 8/2002 | Khalr et al. |
| 2002/0111542 A1 | 8/2002 | Warkentin et al. |
| 2002/0116042 A1 | 8/2002 | Boling |
| 2002/0126036 A1 | 9/2002 | Flaherty et al. |
| 2002/0147388 A1 | 10/2002 | Mass et al. |
| 2002/0169485 A1 | 11/2002 | Pless et al. |
| 2003/0004428 A1 | 1/2003 | Pless |
| 2003/0009207 A1 | 1/2003 | Paspa et al. |
| 2003/0013981 A1 | 1/2003 | Gevins et al. |
| 2003/0018367 A1 | 1/2003 | DiLorenzo |
| 2003/0028072 A1 | 2/2003 | Fischell et al. |
| 2003/0050549 A1 | 3/2003 | Sochor |
| 2003/0050730 A1 | 3/2003 | Greeven et al. |
| 2003/0073917 A1 | 4/2003 | Echauz et al. |
| 2003/0074033 A1 | 4/2003 | Pless et al. |
| 2003/0083716 A1 | 5/2003 | Nicolelis et al. |
| 2003/0114886 A1 | 6/2003 | Gluckman et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0149457 A1 | 8/2003 | Tcheng et al. |
| 2003/0158587 A1 | 8/2003 | Esteller et al. |
| 2003/0167078 A1 | 9/2003 | Weisner et al. |
| 2003/0174554 A1 | 9/2003 | Dunstone et al. |
| 2003/0176806 A1 | 9/2003 | Pineda et al. |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2004/0034368 A1 | 2/2004 | Pless et al. |
| 2004/0039427 A1 | 2/2004 | Barrett et al. |
| 2004/0039981 A1 | 2/2004 | Riedl et al. |
| 2004/0054297 A1 | 3/2004 | Wingeier et al. |
| 2004/0059761 A1 | 3/2004 | Hively |
| 2004/0068199 A1 | 4/2004 | Echauz et al. |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fischell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138579 A1 | 7/2004 | Deadwyler et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0169723 A1* | 9/2004 | Kawasaki et al. .......... 348/14.01 |
| 2004/0172089 A1 | 9/2004 | Whitehurst et al. |
| 2004/0176359 A1 | 9/2004 | Wermeling |
| 2004/0181263 A1 | 9/2004 | Balzer et al. |
| 2004/0199212 A1 | 10/2004 | Fischell |
| 2004/0210269 A1 | 10/2004 | Shalev et al. |
| 2004/0243146 A1 | 12/2004 | Chesbrough et al. |
| 2004/0267152 A1 | 12/2004 | Pineda et al. |
| 2005/0004621 A1 | 1/2005 | Boveja et al. |
| 2005/0010113 A1* | 1/2005 | Hall et al. .................... 600/473 |
| 2005/0010261 A1 | 1/2005 | Luders et al. |
| 2005/0010864 A1* | 1/2005 | Horikiri et al. .............. 715/511 |
| 2005/0015128 A1 | 1/2005 | Rezai et al. |
| 2005/0015129 A1 | 1/2005 | Mische |
| 2005/0021105 A1 | 1/2005 | Firlik et al. |
| 2005/0021108 A1 | 1/2005 | Klosterman et al. |
| 2005/0021313 A1 | 1/2005 | Nikitin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0043774 A1 | 2/2005 | Devlin et al. |
| 2005/0049649 A1 | 3/2005 | Luders et al. |
| 2005/0059867 A1 | 3/2005 | Cheng |
| 2005/0070970 A1 | 3/2005 | Knudson et al. |
| 2005/0075067 A1 | 4/2005 | Lawson et al. |
| 2005/0096710 A1 | 5/2005 | Kieval |
| 2005/0113885 A1 | 5/2005 | Haubrich et al. |
| 2005/0124863 A1 | 6/2005 | Cook |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0182308 A1 | 8/2005 | Bardy |
| 2005/0182464 A1 | 8/2005 | Schulte et al. |
| 2005/0187789 A1 | 8/2005 | Hatlestad |
| 2005/0197590 A1 | 9/2005 | Osorio et al. |
| 2005/0203366 A1 | 9/2005 | Donoghue et al. |
| 2005/0203584 A1 | 9/2005 | Twetan et al. |
| 2005/0209218 A1 | 9/2005 | Meyerson et al. |
| 2005/0222503 A1 | 10/2005 | Dunlop et al. |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240245 A1 | 10/2005 | Bange et al. |
| 2005/0245970 A1 | 11/2005 | Erickson et al. |
| 2005/0245971 A1 | 11/2005 | Brockway et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0094970 A1 | 5/2006 | Drew |
| 2006/0111644 A1 | 5/2006 | Guttag et al. |
| 2006/0122469 A1 | 6/2006 | Martel |
| 2006/0129056 A1 | 6/2006 | Leuthardt et al. |
| 2006/0142822 A1 | 6/2006 | Tulgar |
| 2006/0173259 A1 | 8/2006 | Flaherty et al. |
| 2006/0173510 A1 | 8/2006 | Besio et al. |
| 2006/0200038 A1 | 9/2006 | Savit et al. |
| 2006/0212092 A1 | 9/2006 | Pless et al. |
| 2006/0212093 A1 | 9/2006 | Pless et al. |
| 2006/0212096 A1 | 9/2006 | Stevenson |
| 2006/0217792 A1 | 9/2006 | Hussein et al. |
| 2006/0224191 A1 | 10/2006 | Dilorenzo |
| 2006/0253096 A1 | 11/2006 | Blakley et al. |
| 2006/0293578 A1 | 12/2006 | Rennaker, II |
| 2006/0293720 A1 | 12/2006 | DiLorenzo et al. |
| 2007/0027367 A1 | 2/2007 | Oliver et al. |
| 2007/0027514 A1 | 2/2007 | Gerber |
| 2007/0035910 A1 | 2/2007 | Stevenson |
| 2007/0043459 A1 | 2/2007 | Abbott, III et al. |
| 2007/0055320 A1 | 3/2007 | Weinand |
| 2007/0060973 A1 | 3/2007 | Ludvig et al. |
| 2007/0073355 A1 | 3/2007 | DiLorenzo |
| 2007/0073357 A1 | 3/2007 | Rooney et al. |
| 2007/0100398 A1 | 5/2007 | Sloan |
| 2007/0149952 A1 | 6/2007 | Bland et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0167991 A1 | 7/2007 | DiLorenzo |
| 2007/0185890 A1 | 8/2007 | VanEpps et al. |

(56) References Cited

U.S. PATENT DOCUMENTS

| | | | |
|---|---|---|---|
| 2007/0213629 A1 | 9/2007 | Greene | |
| 2007/0213785 A1* | 9/2007 | Osorio et al. | 607/45 |
| 2007/0217121 A1 | 9/2007 | Fu et al. | |
| 2007/0238939 A1 | 10/2007 | Giftakis et al. | |
| 2007/0244407 A1 | 10/2007 | Osorlo | |
| 2007/0250077 A1 | 10/2007 | Skakoon et al. | |
| 2007/0250901 A1 | 10/2007 | McIntire et al. | |
| 2007/0287931 A1 | 12/2007 | DiLorenzo | |
| 2008/0021341 A1 | 1/2008 | Harris et al. | |
| 2008/0027347 A1 | 1/2008 | Harris et al. | |
| 2008/0027348 A1 | 1/2008 | Harris et al. | |
| 2008/0027515 A1 | 1/2008 | Harris et al. | |
| 2008/0033502 A1 | 2/2008 | Harris et al. | |
| 2008/0082019 A1 | 4/2008 | Ludving et al. | |
| 2008/0091090 A1 | 4/2008 | Guillory et al. | |
| 2008/0103556 A1 | 5/2008 | Li et al. | |
| 2008/0114417 A1 | 5/2008 | Leyde | |
| 2008/0119900 A1 | 5/2008 | DiLorenzo | |
| 2008/0161712 A1 | 7/2008 | Leyde | |
| 2008/0161713 A1 | 7/2008 | Leyde et al. | |
| 2008/0163085 A1* | 7/2008 | Subbu et al. | 715/763 |
| 2008/0183096 A1* | 7/2008 | Snyder et al. | 600/545 |
| 2008/0183097 A1 | 7/2008 | Leyde et al. | |
| 2008/0208074 A1 | 8/2008 | Snyder et al. | |
| 2008/0221876 A1 | 9/2008 | Holdrich | |
| 2008/0255582 A1 | 10/2008 | Harris | |
| 2008/0273287 A1 | 11/2008 | Iyer et al. | |
| 2008/0319281 A1 | 12/2008 | Aarts | |
| 2009/0018609 A1 | 1/2009 | DiLorenzo | |
| 2009/0062682 A1 | 3/2009 | Bland et al. | |
| 2009/0062696 A1 | 3/2009 | Nathan et al. | |
| 2009/0171168 A1 | 7/2009 | Leyde et al. | |
| 2009/0171420 A1 | 7/2009 | Brown et al. | |
| 2009/0264952 A1 | 10/2009 | Jassemidis et al. | |
| 2009/0290971 A1* | 11/2009 | Shamseldin et al. | 415/1 |
| 2010/0023089 A1 | 1/2010 | DiLorenzo | |
| 2010/0125219 A1 | 5/2010 | Harris et al. | |
| 2010/0145176 A1 | 6/2010 | Himes | |
| 2010/0168603 A1 | 7/2010 | Himes et al. | |
| 2010/0168604 A1 | 7/2010 | Echauz et al. | |
| 2010/0179627 A1 | 7/2010 | Floyd et al. | |
| 2010/0217348 A1 | 8/2010 | DiLorenzo | |
| 2010/0265072 A1* | 10/2010 | Goetz et al. | 340/573.1 |
| 2011/0166430 A1 | 7/2011 | Harris et al. | |
| 2011/0172554 A1 | 7/2011 | Leyde et al. | |
| 2011/0201944 A1 | 8/2011 | Higgins et al. | |
| 2011/0213222 A1 | 9/2011 | Leyde et al. | |
| 2011/0218820 A1 | 9/2011 | Himes et al. | |
| 2011/0219325 A1 | 9/2011 | Himes et al. | |
| 2011/0260855 A1 | 10/2011 | John et al. | |
| 2011/0319785 A1 | 12/2011 | Snyder et al. | |

FOREIGN PATENT DOCUMENTS

| | | |
|---|---|---|
| CA | 2428116 | 5/2002 |
| CA | 2428383 | 5/2002 |
| CA | 2425122 | 6/2002 |
| CA | 2425004 | 8/2002 |
| CA | 2456443 | 1/2003 |
| CA | 2491987 | 1/2004 |
| DE | 69832022D | 12/2005 |
| EP | 0124663 A1 | 11/1984 |
| EP | 0898460 | 3/1999 |
| EP | 1145735 A2 | 10/2001 |
| EP | 1145736 A2 | 10/2001 |
| EP | 1307260 | 5/2003 |
| EP | 1335668 | 8/2003 |
| EP | 1525551 | 4/2005 |
| EP | 0911061 B1 | 10/2005 |
| EP | 1609414 A2 | 12/2005 |
| JP | 24033673 A2 | 2/2004 |
| SU | 1074484 | 2/1984 |
| WO | WO 85/01213 A1 | 3/1985 |
| WO | WO 92/00119 A1 | 1/1992 |
| WO | WO 97/26823 A1 | 7/1997 |
| WO | WO 97/34522 A1 | 9/1997 |
| WO | WO 97/34524 A1 | 9/1997 |
| WO | WO 97/34525 A1 | 9/1997 |
| WO | WO 97/39797 A1 | 10/1997 |
| WO | WO 97/42990 A1 | 11/1997 |
| WO | WO 97/45160 A1 | 12/1997 |
| WO | WO 98/49935 A1 | 11/1998 |
| WO | WO 99/20342 A1 | 4/1999 |
| WO | WO 99/56821 A1 | 11/1999 |
| WO | WO 99/56822 A1 | 11/1999 |
| WO | WO 00/07494 A2 | 2/2000 |
| WO | WO 00/10455 | 3/2000 |
| WO | WO 01/41867 A1 | 6/2001 |
| WO | WO 01/48676 A1 | 7/2001 |
| WO | WO 01/49364 A2 | 7/2001 |
| WO | WO 01/67288 A2 | 9/2001 |
| WO | WO 01/75660 A1 | 10/2001 |
| WO | WO 02/09610 A1 | 2/2002 |
| WO | WO 02/09811 A1 | 2/2002 |
| WO | WO 02/36003 A1 | 5/2002 |
| WO | WO 02/38031 A2 | 5/2002 |
| WO | WO 02/38217 A2 | 5/2002 |
| WO | WO 02/49500 A2 | 6/2002 |
| WO | WO 02/058536 A2 | 8/2002 |
| WO | WO 02/067122 A1 | 8/2002 |
| WO | WO 03/001996 A2 | 1/2003 |
| WO | WO 03/009207 A1 | 1/2003 |
| WO | WO 03/030734 A2 | 4/2003 |
| WO | WO 03/035165 A1 | 5/2003 |
| WO | WO 03/084605 A1 | 10/2003 |
| WO | WO 2004/008373 A2 | 1/2004 |
| WO | WO 2004/032720 A2 | 4/2004 |
| WO | WO 2004/034231 A2 | 4/2004 |
| WO | WO 2004/034879 A2 | 4/2004 |
| WO | WO 2004/034880 A2 | 4/2004 |
| WO | WO 2004/034881 A2 | 4/2004 |
| WO | WO 2004/034882 A2 | 4/2004 |
| WO | WO 2004/034885 A2 | 4/2004 |
| WO | WO 2004/034982 A2 | 4/2004 |
| WO | WO 2004/034997 A2 | 4/2004 |
| WO | WO 2004/034998 A2 | 4/2004 |
| WO | WO 2004/035130 A2 | 4/2004 |
| WO | WO 2004/036370 A2 | 4/2004 |
| WO | WO 2004/036372 A2 | 4/2004 |
| WO | WO 2004/036376 A2 | 4/2004 |
| WO | WO 2004/036377 A2 | 4/2004 |
| WO | WO 20041034883 | 4/2004 |
| WO | WO 2004/037342 A2 | 5/2004 |
| WO | WO 2004/043536 A1 | 5/2004 |
| WO | WO 2004/091718 A1 | 10/2004 |
| WO | WO 2005/007236 A2 | 1/2005 |
| WO | WO 2005/028026 A1 | 3/2005 |
| WO | WO 2005/028028 A1 | 3/2005 |
| WO | WO 2005/031630 A2 | 4/2005 |
| WO | WO 2005/051167 A1 | 6/2005 |
| WO | WO 2005/051306 A2 | 6/2005 |
| WO | WO 2005/117693 A1 | 12/2005 |
| WO | WO 2006/014971 A2 | 2/2006 |
| WO | WO 2006/014972 A2 | 2/2006 |
| WO | WO 2006/020794 A2 | 2/2006 |
| WO | WO2006/035392 A1 | 4/2006 |

OTHER PUBLICATIONS

Adjouadi, et al. A new mathematical approach based on orthogonal operators for the detection of interictal spikes in epileptogenic data. Biomed. Sci. Instrum. 2004; 40: 175-80.

Adjouadi, et al. Detection of interictal spikes and artifactual data through orthogonal transformations. J. Clin. Neurophysiol. 2005; 22(1):53-64.

Adjouadi, et al. Interictal spike detection using the Walsh transform. IEEE Trans. Biomed. Eng. 2004; 51(5): 868-72.

Aksenova, et al. Nonparametric on-line detection of changes in signal spectral characteristics for early prediction of epilepsy seizure onset. J. Automation and Information Sciences. 2004; 36(8): 35-45.

Aksenova, et al. On-line disharmony detection for early prediction of epilepsy seizure onset. 5th International Workshop Neural Coding 2003. Aulla (Italy) Sep. 20-25, 2003. (Abstract).

(56) References Cited

OTHER PUBLICATIONS

Andrzejak, et al. Bivariate surrogate techniques: necessity, strengths, and caveats. Physical Review E. 2003; 68: 066202-1-066202-15.

Andrzejak, et al. Testing the null hypothesis of the nonexistence of a preseizure state. Physical Review E. 2003; 67: 010901-1-010901-4.

Aschenbrenner-Scheibe, et al. How well can epileptic seizures be predicted? An evaluation of a nonlinear method. Brain. 2003; 126: 2616-26.

Bangham et al. Diffusion of univalent ions across the lamellae of swollen phospholipids. 1965. J Mol. Biol. 13: 238-252.

Baruchi, et al. Functional holography of complex networks activity—From cultures to the human brain. Complexity. 2005; 10(3): 38 R 51.

Baruchi, et al. Functional holography of recorded neuronal networks activity. Neuroinformatics. 2004; 2(3): 333-51.

Ben-Hur, et al. Detecting stable clusters using principal component analysis. Methods Mol. Biol. 2003; 224: 159-82.

Bergey, et al. Epileptic seizures are characterized by changing signal complexity. Clin. Neurophysiol. 2001; 112(2): 241-9.

Betterton, et al. Determining State of Consciousness from the Intracranial Electroencephalogram (IEEG) for Seizure Prediction. From Proceeding (377) Modeling, Identification, and Control. 2003; 377-201: 313-317.

Bhattacharya, et al. Enhanced phase synchrony in the electroencephalograph gamma band for musicians while listening to music. Phys. Rev. E. 2001; 64:012902-1-4.

Boley, et al. Training Support Vector Machine using Adaptive Clustering. 2004 SIAM International Conference on Data Mining, Apr. 22-Apr. 24, 2004. Lake Buena Vista, FL, USA. 12 pages.

Burges, C. A Tutorial on Support Vector Machines for Pattern Recognition. Data Mining and Knowledge Discovery. 1998; 2: 121-167.

Cao, et al. Detecting dynamical changes in time series using the permutation entropy. Physical Review E. 2004; 70:046217-1-046217-7.

Carretero-Gonzalez, et al. Scaling and interleaving of subsystem Lyapunov exponents for spatio-temporal systems. Chaos. 1999; 9(2): 466-482.

Casdagli, et al. Characterizing nonlinearity in invasive EEG recordings from temporal lobe epilepsy. Physica D. 1996; 99 (2/3): 381-399.

Casdagli, et al. Nonlinear Analysis of Mesial Temporal Lobe Seizures Using a Surrogate Data Technique. Epilepsia. 1995; 36, suppl. 4, pp. 142.

Casdagli, et al. Non-linearity in invasive EEG recordings from patients with temporal lobe epilepsy. Electroencephalogr. Clin. Neurophysiol. 1997; 102(2): 98-105.

Cerf, et al. Criticality and synchrony of fluctuations in rhythmical brain activity: pretransitional effects in epileptic patients. Biol. Cybern. 2004; 90(4): 239-55.

Chaovalitwongse et al.; Reply to comments on "Performance of a seizure warning based on the dynamics of intracranial EEG"; Epilepsy Research, Elsevier Science Publishers, Amsterdam, NL; vol. 72; No. 1; pp. 82-84; Nov. 1, 2006.

Chaovalitwongse, et al. EEG Classification in Epilepsy. Annals. 2004; 2 (37): 1-31.

Chaovalitwongse, et al. Performance of a seizure warning algorithm based on the dynamics of intracranial EEG. Epilepsy Res. 2005; 64(3): 93-113.

Chavez, et al. Spatio-temporal dynamics prior to neocortical seizures: amplitude versphase couplings. IEEE Trans. Biomed. Eng. 2003; 50(5):571-83.

Chen et al.; Clinical utility of video-EEG monitoring; Pediatric Neurology; vol. 12; No. 3; pp. 220-224; 1995.

Crichton, Michael, "Terminal Man", 1972, Ballantine Books, NY, NY, pp. 21-24, 32-33, 70-71, and 74-81.

D'Alessandro, et al. A multi-feature and multi-channel univariate selection process for seizure prediction. Clin. Neurophysiol. 2005; 116(3): 506-16.

D'Alessandro, et al. Epileptic seizure prediction using hybrid feature selection over multiple Intracranial EEG electrode contacts: a report of four patients. IEEE Trans. Biomed. Eng. 2003; 50(5): 603-15.

Drury, et al. Seizure prediction using scalp electroencephalogram. Exp. Neurol. 2003; 184 Suppl 1: S9-18.

Ebersole, J. S. Functional neuroimaging with EEG source models to localize epileptogenic foci noninvasively. Neurology, Available at http://www.uchospitals.edu/pdf/uch_001471.pdf. Accessed Feb. 28, 2006.

Ebersole, J. S. In search of seizure prediction: a critique. Clin. Neurophysiol. 2005; 116(3): 489-92.

Elbert et al. Chaos and Physiology: Deterministic Chaos in Excitable Cell Assemblies. Physiological Reviews. 1994; 74(1):1-47.

Elger, et al. Nonlinear EEG analysis and its potential role in epileptology. Epilepsia. 2000; 41 Suppl 3: S34-8.

Elger, et al. Seizure prediction by non-linear time series analysis of brain electrical activity. Eur. J. Neurosci. 1998; 10(2): 786-789.

Esteller, et al. A Comparison of Waveform Fractal Dimension Algorithms. IEEE Transactions on Circuits and Systems. 2001; vol. 48(2): 177-183.

Esteller, et al. Continuoenergy variation during the seizure cycle: towards an on-line accumulated energy. Clin. Neurophysiol. 2005; 116(3): 517-26.

Esteller, et al. Feature Parameter Optimization for Seizure Detection/prediction. Proceedings of the 23rd Annual International Conference of the IEEE Engineering in Medicine and Biology Society, Istanbul, Turkey. Oct. 2001.

Faul, et al. An evaluation of automated neonatal seizure detection methods. Clin. Neurophysiol. 2005; 116(7): 1533-41.

Fein, et al. Common reference coherence data are confounded by power and phase effects. Electroencephalogr. Clin. Neurophysiol. 1988; 69:581-584.

Fell, et al. Linear inverse filtering improves spatial separation of nonlinear brain dynamics: a simulation study. J. Neurosci. Methods. 2000; 98(1): 49-56.

Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.

Fisher et al. 1999. Reassessment: Vagnerve stimulation for epilepsy, A report of the therapeutics and technology assessment subcommitte of the American Academy of Neurology. Neurology.53: 666-669.

Franaszczuk et al.; An autoregressive method for the measurement of synchronization of interictal and ictal EEG signals; Biological Cybernetics, vol. 81; No. 1; pp. 3-9; 1999.

Gardner, A. B. A Novelty Detection Approach to Seizure Analysis from Intracranial EEG. Georgia Institute of Technology. Apr. 2004. A dissertation available at http://etd.gatech.edu/theses /available/etd-04122004-132404/unrestricted/gardner _andrew_b_200405 _phd.pdf. Accessed Feb. 28, 2006.

Geva, et al. Forecasting generalized epileptic seizures from the EEG signal by wavelet analysis and dynamic unsupervised fuzzy clustering. IEEE Trans. Biomed. Eng. 1998; 45(10): 1205-16.

Gigola, et al. Prediction of epileptic seizures using accumulated energy in a multiresolution framework. J. Neurosci. Methods. 2004; 138(1-2): 107-111.

Guyon, I. An introduction to variable and feature selection. Journal of Machine Learning Research. 2003; 3:1157-1182.

Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.

Harrison, et al. Accumulated energy revised. Clin. Neurophysiol. 2005; 116 (3):527-31.

Harrison, et al. Correlation dimension and integral do not predict epileptic seizures. Chaos. 2005; 15(3): 33106-1-15.

Hearst M. Trends & Controversies: Support Vector Machines. IEEE Intelligent Systems. 1998; 13: 18-28.

Hively, et al. Channel-consistent forewarning of epileptic events from scalp EEG. IEEE Trans. Biomed. Eng. 2003; 50(5): 584-93.

Hively, et al. Detecting dynamical changes in nonlinear time series. Physics Letters A. 1999; 258: 103-114.

Hively, et al. Epileptic Seizure Forewarning by Nonlinear Techniques. ORNL/TM-2000/333 Oak Ridge National Laboratory. Nov.

(56) References Cited

OTHER PUBLICATIONS

2000. Available at http://computing.oml.gov/cse_home/staff/hively/NBICradaAnnualRpt FY00.pdf. Accessed Feb. 28, 2006.
Hjorth, B. Source derivation simplifies topographical EEG interpretation. Am. J. EEG Technol. 1980; 20: 121-132.
Hsu, et al. A practical guide to support vector classification. Technical report, Department of Computer Science and Information Technology, National Taiwan University, 2003. Available at http://www.csie.ntu.edu.tw/~cjlin/papers/guide/guide.pdf. Accessed Feb. 28, 2006.
Huynh, J. A. Evaluation of Gene Selection Using Support Vector Machine Recursive Feature Elimination. Arizona State University. May 26, 2004. (28 pages).
Huynh, J. A. Evaluation of Gene Selection Using Support Vector Machine Recursive Feature Elimination. Presentation slides. (41 pages) (May 26, 2004).
Iasemidis, et al. Adaptive epileptic seizure prediction system. IEEE Trans. Biomed. Eng. 2003; 50(5):616-27.
Iasemidis, et al. Automated Seizure Prediction Paradigm. Epilepsia. 1998; vol. 39, pp. 56.
Iasemidis, et al, Chaos Theory and Epilepsy. The Neuroscientist. 1996; 2:118-126.
Iasemidis, et al. Comment on "Inability of Lyapunov exponents to predict epileptic seizures." Physical Review Letters. 2005; 94(1):019801-1.
Iasemidis, et al. Detection of the Preictal Transition State in Scalp-Sphenoidal EEG Recordings. American Clinical Neurophysiology Society Annual Meeting, Sep. 1996. pp. C206.
Iasemidis, et al. Dynamical Interaction of the Epileptogenic Focwith Extrafocal Sites in Temporal Lobe Epilepsy (TLE). Ann. Neurol. 1997; 42, pp. 429. pp. M146.
Iasemidis, et al. Epileptogenic FocLocalization by Dynamical Analysis of Interictal Periods of EEG in Patients with Temporal Lobe Epilepsy. Epilepsia. 1997; 38, suppl. 8, pp. 213.
Iasemidis, et al. Localizing Preictal Temporal Lobe Spike Foci Using Phase Space Analysis. Electroencephalography and Clinical Neurophysiology. 1990; 75, pp. S63-64.
Iasemidis, et al. Long-term prospective on-line real-time seizure prediction. Clin. Neurophysiol. 2005; 116(3):532-44.
Iasemidis, et al. Long-Time-Scale Temporo-spatial Patterns of Entrainment of Preictal Electrocorticographic Data in Human Temporal Lobe Epilepsy. Epilepsia. 1990; 31(5):621.
Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.
Iasemidis, et al. Modelling of ECoG in temporal lobe epilepsy. Biomed. Sci. Instrum. 1988; 24: 187-93.
Iasemidis, et al. Nonlinear Dynamics of EcoG Data in Temporal Lobe Epilepsy. Electroencephalography and Clinical Neurophysiology. 1998; 5, pp. 339.
Iasemidis, et al. Phase space topography and the Lyapunov exponent of electrocorticograms in partial seizures. Brain Topogr. 1990; 2(3): 187-201.
Iasemidis, et al. Preictal Entrainment of a Critical Cortical Mass is a Necessary Condition for Seizure Occurrence. Epilepsia. 1996; 37, suppl. 5. pp. 90.
Iasemidis, et al. Preictal-Postictal Versus Postictal Analysis for Epileptogenic Focus Localization. J. Clin. Neurophysiol. 1997; 14, pp. 144.
Iasemidis, et al. Quadratic binary programming and dynamic system approach to determine the predictability of epileptic seizures. Journal of Combinatorial Optimization. 2001; 5: 9-26.
Iasemidis, et al. Quantification of Hidden Time Dependencies in the EEG within the Framework of Non-Linear Dynamics. World Scientific. 1993; pp. 30-47.
Iasemidis, et al. Spatiotemporal dynamics of human epileptic seizures. World Scientific. 1996; pp. 26-30.
Iasemidis, et al. Spatiotemporal Evolution of Dynamical Measures Precedes Onset of Mesial Temporal Lobe Seizures. Epilepsia. 1994; 358, pp. 133.
Iasemidis, et al. Spatiotemporal Transition to Epileptic Seizures: A Nonlinear Dynamical Analysis of Scalp and Intracranial EEG Recordings. (In SILVA, F.L. Spatiotemporal Models in Biological and Artificial Systems. Ohmsha IOS Press. 1997; 37, pp. 81-88.).
Iasemidis, et al. The evolution with time of the spatial distribution of the largest Lyapunov exponent on the human epileptic cortex. World Scientific. 1991; pp. 49-82.
Iasemidis, et al. The Use of Dynamical Analysis of EEG Frequency Content in Seizure Prediction. American Electroencephalographic Society Annual Meeting, Oct. 1993.
Iasemidis, et al. Time Dependencies in Partial Epilepsy. 1993; 34, pp. 130-131.
Iasemidis, et al. Time dependencies in the occurrences of epileptic seizures. Epilepsy Res. 1994; 17(1): 81-94.
Iasemidis, L. D. Epileptic seizure prediction and control. IEEE Trans. Biomed. Eng. 2003; 50(5):549-58.
Jerger, et al. Early seizure detection. Journal of Clin. Neurophysiol. 2001; 18(3):259-68.
Jerger, et al. Multivariate linear discrimination of seizures. Clin. Neurophysiol. 2005; 116(3):545-51.
Jouny, et al. Characterization of epileptic seizure dynamics using Gabor atom density. Clin. Neurophysiol. 2003; 114(3):426-37.
Jouny, et al. Signal complexity and synchrony of epileptic seizures: is there an identifiable preictal period? Clin. Neurophysiol. 2005; 116(3):552-8.
Kapiris, et al. Similarities in precursory features in seismic shocks and epileptic seizures. Europhys. Lett. 2005; 69(4):657-663.
Katz, et al. Does interictal spiking change prior to seizures? Electroencephalogr. Clin. Neurophysiol. 1991; 79(2):153-6.
Kerem, et al. Forecasting epilepsy from the heart rate signal. Med. Biol. Eng. Comput. 2005; 43(2):230-9.
Khalilov, et al. Epileptogenic actions of GABA and fast oscillations in the developing hippocampus. Neuron. 2005; 48(5):787-96.
Korn, et al. Is there chaos in the brain? II. Experimental evidence and related models. C. R. Biol. 2003; 326(9):787-840.
Kraskov, A. Synchronization and Interdependence Measures and Their Application to the Electroencephalogram of Epilepsy Patients and Clustering of Data. Available at http://www.kfa-juelich.de/nic-series/volume24/nic-series-band24.pdf. Accessed Apr. 17, 2006 (106 pp).
Kreuz, et al. Measure profile surrogates: a method to validate the performance of epileptic seizure prediction algorithms. Phys. Rev. E. 2004; 69(6 Pt 1):061915-1-9.
Lachaux, et al. Measuring phase synchrony in brain signals. Hum. Brain Mapp. 1999; 8(4):194-208.
Lai, et al. Controlled test for predictive power of Lyapunov exponents: their inability to predict epileptic seizures. Chaos. 2004; 14(3):630-42.
Lai, et al. Inability of Lyapunov exponents to predict epileptic seizures. Phys. Rev. Lett. 2003; 91(6):068102-1-4.
Latka, et al. Wavelet analysis of epileptic spikes. Phys. Rev. E. 2003; 67(5 Pt 1):052902 (6 pages).
Le Van Quyen, et al. Anticipating epileptic seizures in real time by a non-linear analysis of similarity between EEG recordings. Neuroreport. 1999; 10(10):2149-55.
Le Van Quyen, et al. Author's second reply. The Lancet. 2003; 361:971.
Le Van Quyen, et al. Comparison of Hilbert transform and wavelet methods for the analysis of neuronal synchrony. J. Neurosci. Methods. 2001; 111(2):83-98.
Le Van Quyen, et al. Nonlinear analyses of interictal EEG map the brain interdependences in human focal epilepsy. Physica D. 1999; 127:250-266.
Le Van Quyen, et al. Preictal state identification by synchronization changes in long-term intracranial EEG recordings. Clin. Neurophysiol. 2005; 116(3):559-68.
Le Van Quyen, M. Anticipating epileptic seizures: from mathematics to clinical applications. C. R. Biol. 2005; 328(2):187-98.
Lehnertz, et al. Nonlinear EEG analysis in epilepsy: Its possible use for interictal focus localization, seizure anticipation, and prevention. J. Clin. Neurophysiol. 2001; 18(3):209-22.
Lehnertz, et al. Seizure prediction by nonlinear EEG analysis. IEEE Eng. Med. Biol. Mag. 2003; 22(1):57-63.

(56) References Cited

OTHER PUBLICATIONS

Lehnertz, et al. The First International Collaborative Workshop on Seizure Prediction: summary and data description. Clin. Neurophysiol. 2005; 116(3):493-505.

Lehnertz, K. Non-linear time series analysis of intracranial EEG recordings in patients with epilepsy—an overview. Int. J. Psychophysiol. 1999; 34(1):45-52.

Lemos, et al. The weighted average reference montage. Electroencephalogr. Clin. Neurophysiol. 1991; 79(5):361-70.

Li, et al. Fractal spectral analysis of pre-epileptic seizures in terms of criticality. J. Neural Eng. 2005; 2(2):11-16.

Li, et al. Linear and nonlinear measures and seizure anticipation in temporal lobe epilepsy. J. Comput. Neurosci. 2003; 15(3):335-45.

Li, et al. Non-linear, non-invasive method for seizure anticipation in focal epilepsy. Math. Biosci. 2003; 186(1):63-77.

Litt, et al. Prediction of epileptic seizures. Lancet Neurol. 2002; 1(1):22-30.

Litt, et al. Seizure prediction and the preseizure period. Curr. Opin. Neurol. 2002; 15(2):173-7.

Maiwald, et al. Comparison of three nonlinear seizure prediction methods by means of the seizure prediction characteristic. Physica D. 2004; 194:357-368.

Mangasarian, et al. Lagrangian Support Vector Machines. Journal of Machine Learning Research. 2001; 1:161-177.

Martinerie, et al. Epileptic seizures can be anticipated by non-linear analysis. Nat. Med. 1998; 4(10):1173-6.

McSharry, et al. Comparison of predictability of epileptic seizures by a linear and a nonlinear method. IEEE Trans. Biomed. Eng. 2003; 50(5):628-33.

McSharry, et al. Linear and non-linear methods for automatic seizure detection in scalp electro-encephalogram recordings. Med. Biol. Eng. Comput. 2002; 40(4):447-61.

McSharry, P. E. Detection of dynamical transitions in biomedical signals using nonlinear methods. Lecture Notes in Computer Science 2004; 3215:483-490.

Meng, et al. Gaussian mixture models of ECoG signal features for improved detection of epileptic seizures. Med. Eng. Phys. 2004; 26(5):379-93.

Mizuno-Matsumoto, et al. Wavelet-crosscorrelation analysis can help predict whether bursts of pulse stimulation will terminate after discharges. Clin. Neurophysiol. 2002; 113(1):33-42.

Mormann et al.; Seizure prediction: the long and winding road; Brain; vol. 130; No. 2; pp. 314-333; Sep. 28, 2006.

Mormann, et al. Automated detection of a preseizure state based on a decrease in synchronization in intracranial electroencephalogram recordings from epilepsy patients. Phys. Rev. E. 2003; 67(2 Pt 1):021912-1-10.

Mormann, et al. Epileptic seizures are preceded by a decrease in synchronization. Epilepsy Res. 2003; 53(3):173-85.

Mormann, et al. Mean phase coherence as a measure for phase synchronization and its application to the EEG of epilepsy patients. Physics D. 2000; 144:358-369.

Mormann, et al. On the predictability of epileptic seizures. Clin. Neurophysiol. 2005; 116(3):569-87.

Mormann, et al. Seizure anticipation: from algorithms to clinical practice. Curr. Opin. Neurol. 2006; 19(2):187-93.

Navarro, et al. Seizure anticipation in human neocortical partial epilepsy. Brain. 2002; 125:640-55.

Navarro, et al. Seizure anticipation: do mathematical measures correlate with video-EEG evaluation? Epilepsia. 2005; 46(3):385-96.

Niederhauser, et al. Detection of seizure precursors from depth-EEG using a sign periodogram transform. IEEE Trans. Biomed. Eng. 2003; 50(4):449-58.

Nigam, et al. A neural-network-based detection of epilepsy. Neurological Research. 2004; 26(1):55-60.

Osorio, et al. Automated seizure abatement in humans using electrical stimulation. Ann. Neurol. 2005; 57(2):258-68.

Osorio, et al. Performance reassessment of a real-time seizure-detection algorithm on long ECoG series. Epilepsia. 2002; 43(12):1522-35.

Osorio, et al. Real-time automated detection and quantitative analysis of seizures and short-term prediction of clinical onset. Epilepsia. 1998; 39(6):615-27.

Ossadtchi, et al. Hidden Markov modelling of spike propagation from interictal MEG data. Phys. Med. Biol. 2005; 50(14):3447-69.

Pflieger, et al. A noninvasive method for analysis of epileptogenic brain connectivity. Presented at the American Epilepsy Society 2004 Annual Meeting, New Orleans. Dec. 6, 2004. Epilepsia. 2004; 45 (Suppl. 7):70-71.

Pittman, V. Flexible Drug Dosing Produces Less Side-effects in People With Epilepsy. Dec. 29, 2005. Available at http://www.medicalnewstoday.com/medicalnews.php?newsid=35478. Accessed on Apr. 17, 2006.

Platt, et al. Large Margin DAGs for Multiclass Classification. S.A. Solla. T.K. Leen adn K. R. Muller (eds.). 2000; pp. 547-553.

Platt, J. C. Using Analytic QP and Sparseness to Speed Training of Support Vector Machines. Advances in Neural Information Processing Systems. 1999; 11:557-563.

Protopopescu, et al. Epileptic event forewarning from scalp EEG. J. Clin. Neurophysiol. 2001; 18(3):223-45.

Rahimi, et al. On the Effectiveness of Aluminum Foil Helmets: An Empirical Study. Available at http://people.csail.mit.edu/rahimi/helmet/. Accessed Mar. 2, 2006.

Rothman et al.; Local Cooling: a therapy for intractable neocortical epilepsy; Epilepsy Currents; vol. 3; No. 5; pp. 153-156; Sep./Oct. 2003.

Robinson, et al. Steady States and Global Dynamics of Electrical Activity in the Cerebral Cortex. Phys. Rev. E. 1998; (58):3557-3571.

Rudrauf, et al. Frequency flows and the time-frequency dynamics of multivariate phase synchronization in brain signals. NeuroImage. 2005. (19 pages.).

Saab, et al. A system to detect the onset of epileptic seizures in scalp EEG. Clin. Neurophysiol, 2005; 116:427-442.

Sackellares et al. Computer-Assisted Seizure Detection Based on Quantitative Dynamical Measures. American Electroencephalographic Society Annual Meeting, Sep. 1994.

Sackellares et al. Dynamical Studies of Human Hippocampin Limbic Epilepsy. Neurology. 1995; 45, Suppl. 4, pp. A 404.

Sackellares et al. Epileptic Seizures as Neural Resetting Mechanisms. Epilepsia. 1997; vol. 38, Sup. 3.

Sackellares et al. Measurement of Chaos to Localize Seizure Onset. Epilepsia. 1989; 30(5):663.

Sackellares et al. Relationship Between Hippocampal Atrophy and Dynamical Measures of EEG in Depth Electrode Recordings. American Electroencephalographic Society Annual Meeting, Sep. 1995. pp. A105.

Sackellares et al.; Predictability analysis for an automated seizure prediction algorithm; Journal of Clinical Neurophysiology; vol. 23; No. 6; pp. 509-520; Dec. 2006.

Sackellares, J. C. Epilepsy—when chaos fails. In: chaos in the brain? Eds. K. Lehnertz & C.E. Elger. World Scientific. 2000 (22 pages).

Salant, et al. Prediction of epileptic seizures from two-channel EEG. Med. Biol. Eng. Comput. 1998; 36(5):549-56.

Schelter et al.; Testing statistical significance of multivariate time series analysis techniques for epileptic seizure prediction; Chaos; vol. 16; pp. 013108-1-10; Jan. 2006.

Schelter, et al. Testing for directed influences among neural signals using partial directed coherence. J. Neurosci. Methods. 2006; 152(1-2):210-9.

Schindler, et al. EEG analysis with simulated neuronal cell models helps to detect pre-seizure changes. Clin. Neurophysiol. 2002; 113(4):604-14.

Schwartzkroin, P. Origins of the Epileptic State. Epilepsia. 1997; 38, supply. 8, pp. 853-858.

Sheridan, T. Humans and Automation. NY: John Wiley. 2002.

Shoeb et al. Patient-specific seizure detection. MIT Computer Science and Artificial Intelligence Laboratory. 2004; pp. 193-194.

Snyder et al; The statistics of a practical seizure warning system; Journal of Neural Engineering; vol. 5; pp. 392-401; 2008.

Staba, et al. Quantitative analysis of high-frequency oscillations (80-500 Hz) recorded in human epileptic hippocampand entorhinal cortex. J. Neurophysiol. 2002; 88(4):1743-52.

(56) References Cited

OTHER PUBLICATIONS

Stefanski, et al. Using chaos synchronization to estimate the largest Lyapunov exponent of nonsmooth systems. Discrete Dynamics in Nature and Society. 2000; 4:207-215.

Subasi, et al. Classification of EEG signals using neural network and logistic regression. Computer Methods Programs Biomed. 2005; 78(2):87-99.

Szoka et al. Procedure for preparation of liposomes with large internal aqueospace and high capture volume by reverse phase evaporation. 1978. Proc. Natl Acad. Sci. USA. 75: 4194-4198.

Tass, et al. Detection of n: m Phase Locking from Noisy Data: Application to Magnetoencephalography. Physical Review Letters. 1998; 81(15):3291-3294.

Terry, et al. An improved algorithm for the detection of dynamical interdependence in bivariate time-series. Biol. Cybern. 2003; 88(2):129-36.

Tetzlaff, et al. Cellular neural networks (CNN) with linear weight functions for a prediction of epileptic seizures. Int"l. J. of Neural Systems. 2003; 13(6):489-498.

Theiler, et al. Testing for non-linearity in time series: the method of surrogate data. Physica D. 1992; 58:77-94.

Tsakalis, K. S. Prediction and control of epileptic seizures: Coupled oscillator models. Arizona State University. (Slide: 53 pages) (No date).

Van Drongelen, et al. Seizure anticipation in pediatric epilepsy: use of Kolmogorov entropy. Pediatr. Neural. 2003; 29(3): 207-13.

Van Putten, M. Nearest neighbor phase synchronization as a measure to detect seizure activity from scalp EEG recordings. J. Clin. Neurophysiol. 2003; 20(5):320-5.

Venugopal, et al. A new approach towards predictability of epileptic seizures: KLT dimension. Biomed Sci. Instrum. 2003; 39:123-8.

Vonck, et al. Long-term amygdalohippocampal stimulation for refractory temporal lobe epilepsy. Ann. Neural, 2002; 52(5):556-65.

Vonck, et al. Long-term deep brain stimulation for refractory temporal lobe epilepsy. Epilepsia. 2005; 46(Suppl 5):98-9.

Vonck, et al. Neurostimulation for refractory epilepsy. Acta. Neurol. Belg. 2003; 103(4):213-7.

Weiss, P. Seizure prelude found by chaos calculation. Science News. 1998; 153(20):326.

Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.

Widman, et al. Reduced signal complexity of intracellular recordings: a precursor for epileptiform activity? Brain Res. 1999; 836(1-2):156-63.

Winterhalder, et al. Sensitivity and specificity of coherence and phase synchronization analysis. (In Press) Phys. Lett. A. 2006.

Winterhalder, et al. The seizure prediction characteristic: a general framework to assess and compare seizure prediction methods. Epilepsy Behav. 2003; 4(3):318-25.

Wong et al.; A stochastic framework for evaluating seizure prediction algorithms using hiden markov models; Journal of Neurophysiology; vol. 97, No. 3; pp. 2525-2532; Oct. 4, 2006.

Yang et al.; Testing whether a prediction scheme is better than guess; Ch. 14 in Quantitative Neuroscience: Models, Algorithms, Diagnostics, and Therapeutic Applications; pp. 251-262; 2004.

Yang, et al. A supervised feature subset selection technique for multivariate time series. Available at http://infolab.usc.edu/DocsDemos/fsdm05.pdf. Accessed Mar. 2, 2006.

Yang, et al. CLe Ver: A feature subset selection technique for multivariate time series. T. B. Ho, D. Cheung, and H. Liu (Eds.): PAKDD. 2005; LNAI 3518: 516-522.

Yang, et al. Relation between Responsiveness to Neurotransmitters and Complexity of Epileptiform Activity in Rat Hippocampal CA1 Neurons. Epilepsia. 2002; 43(11):1330-1336.

Yatsenko, et al. Geometric Models, Fiber Bundles, and Biomedical Applications. Proceedings of Institute of Mathematics of NAS of Ukraine. 2004; 50 (Part 3):1518R1525.

Zaveri et al. Time-Frequency Analyses of Nonstationary Brain Signals. Electroencephalography and Clinical Neurophysiology. 1991; 79, pp. 28P-29P.

Zhang, et al. High-resolution EEG: cortical potential imaging of interictal spikes. Clin. Neurophysiol. 2003; 114(10):1963-73.

Bekas et al.; Low cost high performance uncertainty quantification; Conf. on High Performance Networking and Computing; Portland, Oregon; Article No. 8; (ISBN:978-1-60558-716-.

DiLorenzo, Daniel, U.S. Appl. No. 11/282,317 entitled "Closed-loop vagus nerve stimulation," filed Nov. 17, 2005.

\* cited by examiner

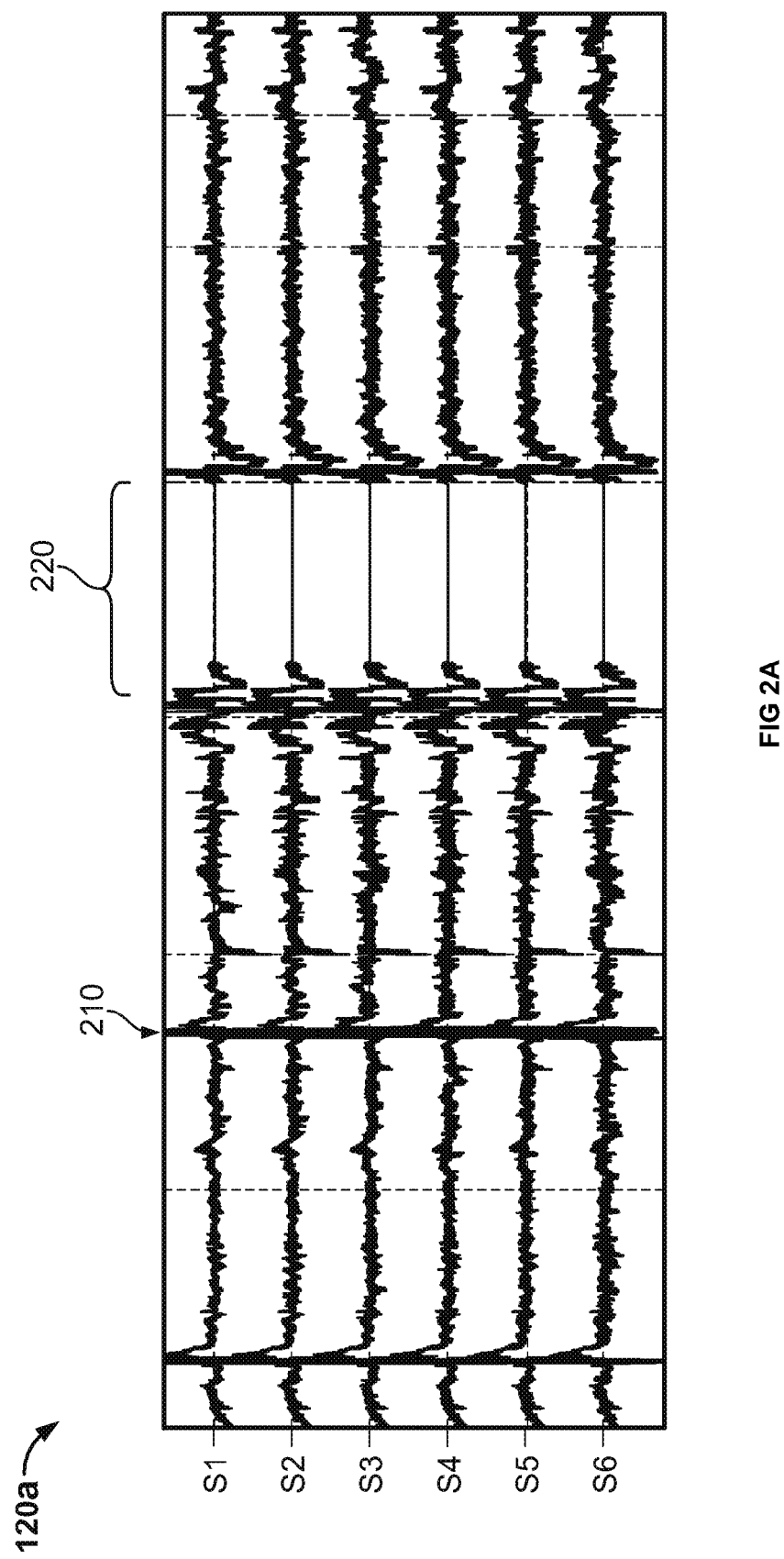

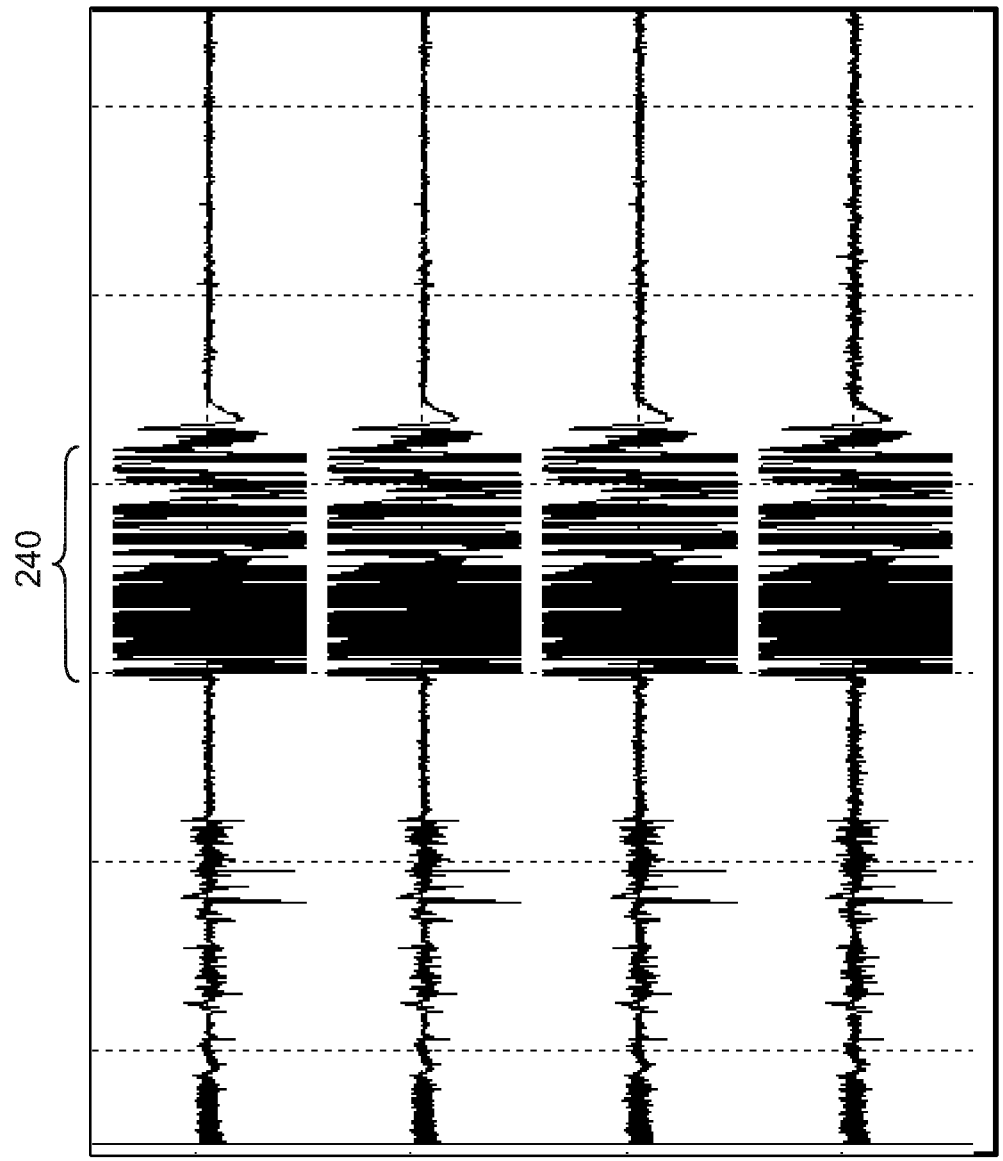

PROCESSING FOR MULTI-CHANNEL SIGNALS

CROSS-REFERENCE TO RELATED APPLICATIONS

This application claims the benefit of U.S. Provisional Application No. 61/183,449, filed Jun. 2, 2009, which is incorporated herein by reference in its entirety.

TECHNICAL FIELD

The present disclosure relates generally to methods for processing multi-channel signals. In particular, the present disclosure relates to improved processing of multi-channel signals by detecting and/or treating possible anomalies in the multi-channel signals

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

A common task encountered in the field of signal processing is the sampling and processing of a physical state using multiple, ideally independent, signal sensors. The diversity of the resulting multi-sensor or multi-channel signal typically reveals more information about the underlying sampled state than can be obtained from employing a single sensor.

Multi-channel signal processing is utilized in biomedical applications. For example, in the field of neurological monitoring for epileptic seizure prediction, multiple electrodes may be implanted in diverse locations on or in a patient's brain to monitor the susceptibility of the patient to enter into an epileptic seizure. The multi-channel signals generated by the electrodes may be processed to, e.g., alert the patient and/or medical personnel of a high likelihood of imminent seizure. See, e.g., U.S. Patent Publication No. 2008/0183096 A1, "Systems and Methods for Identifying a Contra-ictal Condition in a Subject," filed Jan. 25, 2008, assigned to the assignee of the present application, the contents of which are hereby incorporated by reference in their entirety. The signals may also be stored and processed offline to, e.g., train customized algorithms for estimating the likelihood that a patient will experience an imminent seizure. See, e.g., U.S. Pat. No. 6,678,548, "Unified probabilistic framework for predicting and detecting seizure onsets in the brain and multitherapeutic device," the contents of which are hereby incorporated by reference in their entirety.

Other applications of multi-channel signal processing include the reception of wireless signals by a communications device using multiple antennas, geological monitoring of seismic activity for earthquake prediction, stereo imaging using multiple video cameras, etc.

When multi-channel signals are sampled over an extended period of time, artifacts or anomalies often appear in the signal. Such anomalies may be due to interference from external sources, disruptions to the power supply of the sensors, and/or other sources. Left untreated, such anomalies may degrade the quality of the measured signal and disrupt the accuracy of any subsequent processing of the multi-channel signal.

It would be desirable to have techniques to detect the presence of anomalies in a multi-channel signal, and to optimize the processing of a signal containing such anomalies.

SUMMARY OF THE INVENTION

An aspect of the present disclosure provides a method for displaying information associated with a multi-channel signal to a user, the method comprising: accepting input from the user selecting a metric to be displayed; displaying at least one time-series plot of the selected metric associated with the multi-channel signal; using a backdrop pattern, indicating on the at least one time-series plot portions of the plot having at least one identified characteristic; for each of the at least one time-series plot displayed, displaying a time event index wherein the corresponding metric meets a predetermined condition; accepting input from the user as to whether to display further information associated with the time event index; and displaying the further information associated with the time event index if the user so specifies.

Another aspect of the present disclosure provides a method for detecting anomalies in a multi-channel signal, the method comprising: sampling the multi-channel signal over a time window; computing an anomaly metric for the multi-channel signal over the time window; and identifying the presence of an anomaly based on the magnitude of the anomaly metric; the computing an anomaly metric comprising: computing a condition number of the multi-channel signal over the time window; and adjusting the condition number based on a parameter of the multi-channel signal to generate a data condition number (DCN); the identifying the presence of an anomaly comprising comparing the magnitude of the data condition number (DCN) to at least one threshold; the method further comprising generating one of the at least one threshold, the generating comprising: generating a histogram of number of anomalies detected for each of a plurality of candidate thresholds; generating a cumulative distribution function from the histogram, the cumulative distribution function mapping each candidate threshold to a percentage value; and determining the generated threshold as the candidate threshold mapped to a corresponding predetermined percentage value by the cumulative distribution function.

Yet another aspect of the present disclosure provides a method for detecting anomalies in a multi-channel signal, the method comprising: sampling the multi-channel signal over a time window; computing an anomaly metric for the multi-channel signal over the time window; and identifying the presence of an anomaly based on the magnitude of the anomaly metric; the computing an anomaly metric comprising: computing a condition number of the multi-channel signal over the time window; and adjusting the condition number based on a parameter of the multi-channel signal to generate a data condition number (DCN); the identifying the presence of an anomaly comprising comparing the magnitude of the rate of change of the data condition number (DCN) to at least one threshold.

Yet another aspect of the present disclosure provides a method for detecting anomalies in a multi-channel signal, the method comprising: sampling the multi-channel signal over a time window; computing an anomaly metric for the multi-channel signal over the time window; and identifying the presence of an anomaly based on the magnitude of the anomaly metric; the computing an anomaly metric comprising: computing a condition number of the multi-channel signal over the time window; and adjusting the condition number based on a parameter of the multi-channel signal to generate a data condition number (DCN); the multi-channel signal comprising a signal sampled from a plurality of electrodes implanted on or in a patient's brain, the method further comprising: generating a DCN time series corresponding to a plurality of time windows; generating an anomaly log based on the DCN time series; merging anomalies in the anomaly log separated by less than a minimum separation to generate a modified anomaly log; identifying segments of the multi-channel signal corresponding to anomalies in the modified anomaly log; and outputting time-expanded versions of the identified segments to a record; the identifying the presence of an anomaly comprising matching the DCN time series to at least one known pattern of DCN time series corresponding to an anomalous condition.

BRIEF DESCRIPTION OF THE DRAWINGS

FIGS. 2A, 2B and 2C illustrate possible signal anomalies that may be detected by the anomaly detector/processor in the multi-channel signal.

DETAILED DESCRIPTION OF THE INVENTION

The detailed description set forth below in connection with the appended drawings is intended as a description of exemplary embodiments of the present invention and is not intended to represent the only exemplary embodiments in which the present invention can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the invention. It will be apparent to those skilled in the art that the exemplary embodiments of the invention may be practiced without these specific details. In some instances, well known structures and devices are shown in block diagram form in order to avoid obscuring the novelty of the exemplary embodiments presented herein.

While the discussion below focuses on measuring electrical signals generated by electrodes placed near, on, or within the brain or nervous system (EEG signals) of subjects and subject populations for the determination of when an epileptic subject is in a condition susceptible to seizure, it should be appreciated that the techniques of the present disclosure are not limited to measuring EEG signals or to determining when the subject is susceptible to seizure. For example, the techniques could also be used in systems that measure one or more of a blood pressure, blood oxygenation (e.g., via pulse oximetry), temperature of the brain or of portions of the subject, blood flow measurements, ECG/EKG, heart rate signals, respiratory signals, chemical concentrations of neurotransmitters, chemical concentrations of medications, pH in the blood, or other physiological or biochemical parameters of a subject.

The present disclosure may also be applicable to monitoring other neurological or psychiatric disorders and identifying a condition or state for such disorders in which the subject is unlikely to experience some adverse effect. For example, the present disclosure may also be applicable to monitoring and management of sleep apnea, Parkinson's disease, essential tremor, Alzheimer's disease, migraine headaches, depression, eating disorders, cardiac arrhythmias, bipolar spectrum disorders, or the like.

Non-biomedical applications of the techniques described herein are also contemplated to be within the scope of the present disclosure.

Figure 1:
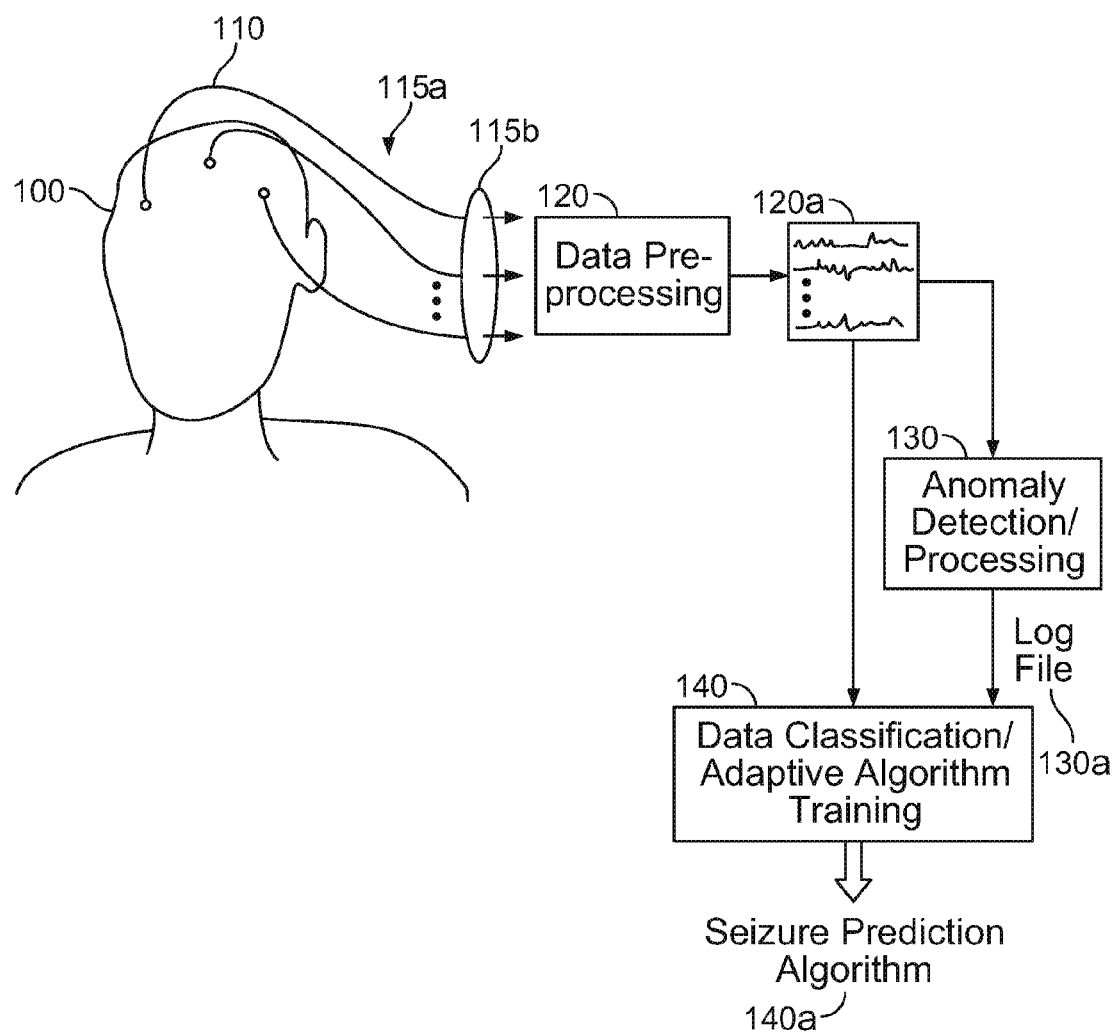
FIG. 1 depicts an exemplary embodiment of the present disclosure of a system for quality management of measured electrical signals generated by electrodes placed on or within the brain.

FIG. 1 depicts an exemplary embodiment of the present disclosure of a system for quality management of measured electrical signals generated by electrodes implanted into the brain, subdurally, epidurally, partially or fully in the skull, between the skull and one or more layers of the patient's scalp, or on the exterior of the patient's head. In some embodiments, the electrodes are configured to be inserted through a single opening in a skull of a patient and to be dispersed on a surface of the brain. The surface is preferably the cortical surface of the brain, but may alternatively be any other suitable surface or layer of the brain, such as the dura mater. Note the exemplary embodiment depicted in FIG. 1 is shown for illustrative purposes only, and is not meant to limit the scope of the present disclosure to any particular embodiment shown.

In FIG. 1, electrodes 110 are implanted on or in the brain of a patient 100, e.g., underneath the dura mater and on a cortical surface of the patient's brain. Each of the electrodes generates a corresponding signal that is input to a data pre-processing module 120. The electrodes may be directly connected to the data pre-processing module 120 through a series of electrical leads 115a, or they may be wirelessly connected to the data pre-processing module 120 over a wireless link. In an exemplary embodiment, data pre-processing module 120 may, e.g., digitize the plurality of received electrical signals 115b to generate a multi-channel signal 120a for further processing.

Multi-channel signal 120a is input to an anomaly detector/processor 130. In an exemplary embodiment, the anomaly detector/processor 130 may utilize techniques further disclosed hereinbelow to identify the presence of signal anomalies in the multi-channel signal 120a. As further disclosed hereinbelow, anomaly detector/processor 130 may also take further action to address the anomalies detected, e.g., flagging the portions of the multi-channel signal corresponding to the detected anomalies in a log file 130a for optional manual review by a human operator.

In the exemplary embodiment shown, the log file 130a from the anomaly detection/processing module 130 is provided along with the multi-channel signal 120a to a data processing/adaptive algorithm training module 140. In an exemplary embodiment, module 140 may utilize the multi-channel signal 120a, coupled with information from the log file 130a about which portions of the multi-channel signal 120a contain anomalies, to train an adaptive algorithm to identify conditions under which patient 100 is susceptible to seizure. An exemplary system is described in Snyder, et al., "The statistics of a practical seizure warning system," *Journal of Neural Engineering*, vol. 5, pp. 392-401 (2008), the contents of which are incorporated by referenced herein in its entirety. In an exemplary embodiment, module 140 may, e.g., automatically de-emphasize portions of multi-channel signal 120a corresponding to signal anomalies, and emphasize other portions of the signal 120a, to configure adaptive weights for a seizure prediction algorithm 140a. In alternative exemplary embodiments, a human operator may manually review portions of multi-channel signal 120a that have been flagged in the log file 130a, and decide whether such portions may be used for adaptive algorithm training.

In an exemplary embodiment, the log file 130a need not be limited to a single file residing in a single piece of storage hardware. For example, the log file 130a can be an extensive archive of intracranial EEG patterns that can be used to develop a predictive neurosensing device for managing seizures by mining the archive for signal patterns over the patient population. This archive may be stored for multi-user access and processing in, e.g., a server or cloud computing system.

Figure 2B:
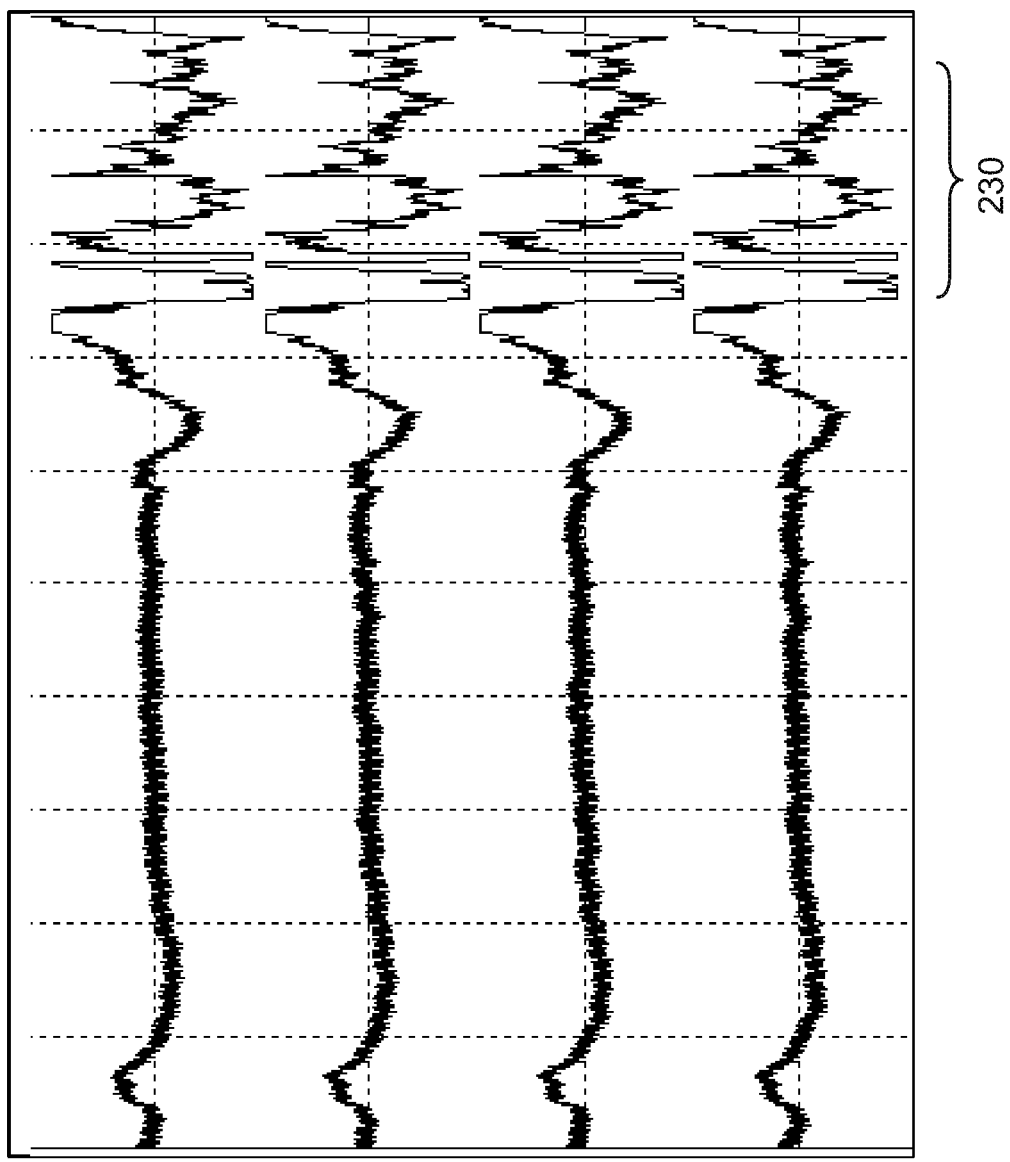

FIGS. 2A, 2B, and 2C illustrate possible signal anomalies that may be detected by the anomaly detector/processor 130 in the multi-channel signal 120a. Note the anomaly patterns identified in FIGS. 2A, 2B, and 2C are for illustrative purposes only, and are not meant to limit the scope of the present disclosure to any particular anomaly patterns highlighted.

In FIG. 2A, reference numeral 210 points to an instance of a "spikes without phase reversal" anomaly in a referential multi-channel signal, or "spikes without double-phase reversal" anomaly in a bipolar multi-channel signal, possibly due to non-physiological interference sources. Reference numeral 220 points to an instance of a "flatline" anomaly in the multi-channel signal. In FIG. 2B, reference numeral 230 points to an instance of a "line noise" anomaly in the multi-channel signal. Such an anomaly may correspond to, e.g., powerline noise, i.e., 50 or 60 Hz noise and/or harmonics superimposed on the multi-channel signal. In FIG. 2C, reference numeral 240 points to an instance of a "saturation" anomaly in the multi-channel signal.

Other possible anomalies in a multi-channel signal (not shown) include episodic artifacts such as motion (large swings in the multi-channel signal), DC shifts (different DC levels between different channels or across a single channel), pops (exponential decay from amplifier highpass characteristic of a sudden change in the DC level of a signal), and glitches (e.g., 50 ms burst transients in the signal). Long-term anomalies may include deterioration trends in the system, and/or channels of persistently poor quality. Such anomalies and others not explicitly enumerated are contemplated to be within the scope of the present disclosure.

Figure 3A:
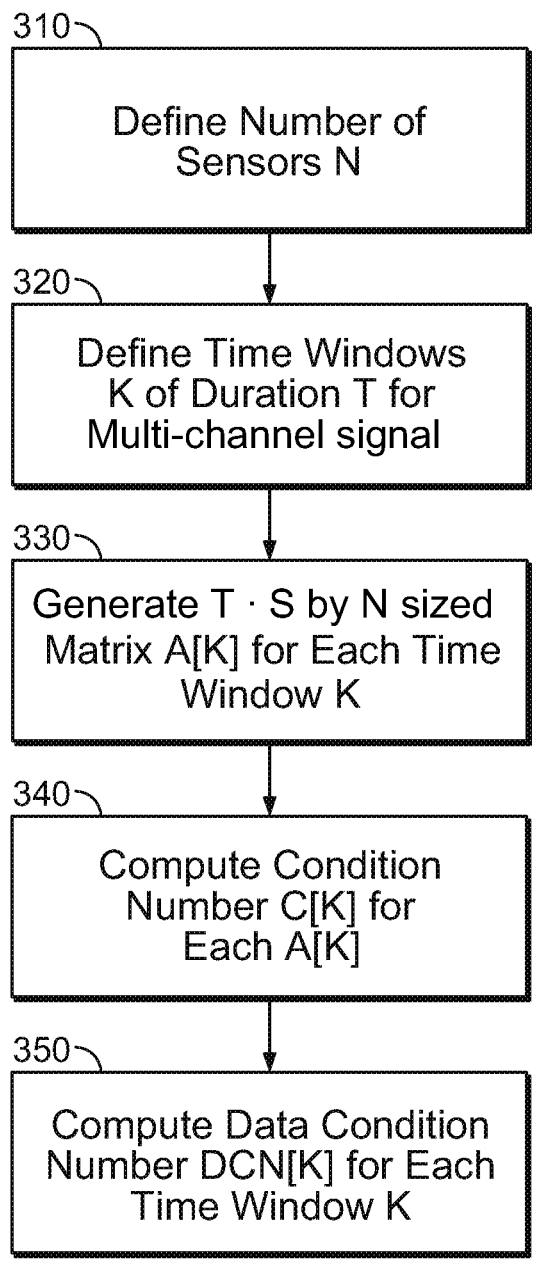
FIG. 3A depicts an exemplary method according to the present disclosure, wherein a metric known as a "data condition number," or DCN, is derived for a given multi-channel signal.

FIG. 3A depicts an exemplary method 300 according to the present disclosure, wherein a specific anomaly metric known as a "data condition number," or DCN, is derived for a given multi-channel signal. In an exemplary embodiment, the DCN may be used to help identify the presence of anomalies in the multi-channel signal. The DCN as described with reference to FIG. 3A has been found to provide a reliable indicator for the presence of anomalies in a multi-channel signal, and is readily applicable to a wide variety of scenarios.

In FIG. 3A, at step 310, the number of dimensions of a multi-channel signal is defined as the variable N. The number of dimensions may correspond to the total number of sensors, e.g., the number of independent electrodes placed in a patient's brain in the epilepsy monitoring system of FIG. 1.

Figure 3B:
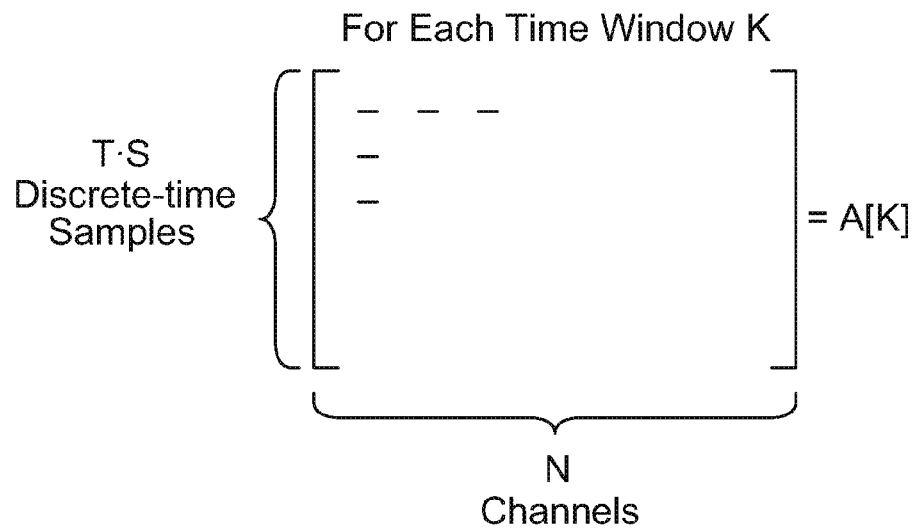
FIG. 3B shows a matrix A[k] derived from the multi-channel signal.

At step 320, the multi-channel signal is divided in time into windows of duration T, with each of the time windows being indexed by a counter k. According to the present disclosure, the multi-channel signal may be a discrete-time signal sampled at a rate of S Hz. In this case, each time window k may contain a total of T·S discrete-time samples multiplied by N channels (or sensors), which may be arranged to form a T·S matrix by N A[k] at step 330. The matrix A[k] is also shown in FIG. 3B. In an exemplary embodiment, the matrix A[k] is generally rectangular.

In an exemplary embodiment, T may be 5 seconds, S may be 400 Hz, and N may be 128 for an epilepsy monitoring unit such as depicted in FIG. 1. In an alternative exemplary embodiment, such as the real-time patient monitoring and neurological event detection system 60 of FIG. 6 utilizing implanted electrodes, N may be 16.

In an exemplary embodiment, the time windows k may be chosen to collectively span the entire duration of the multi-channel signal, i.e., the time windows are non-overlapping and contiguous in time. In alternative exemplary embodiments, the time windows need not be contiguous in time, and may be spread out over the duration of the multi-channel signal. In this way, the time windows effectively sub-sample the total duration of the multi-channel signal. This sub-sampling may result in fewer matrices A[k] to be processed as compared to using contiguous time windows, reducing the computational complexity. In yet other alternative exemplary embodiments, the time windows also may be made overlapping in time. In an exemplary embodiment, the signals for the channels may be represented using a referential montage, wherein each signal is measured as an electrical potential with respect to a common ("ground") contact placed somewhere else in the body; e.g., an "earlobe" in a scalp electroencephalogram.

At step 340, a condition number C[k] is computed for each matrix A[k] as follows:

$$C[k] = \frac{\max\{\sigma_{ik}\}}{\min\{\sigma_{ik}\}};$$ (Equation 1)

wherein $\{\sigma_{ik}\}$ is the set of singular values of each matrix A[k]. In an exemplary embodiment, the singular values of each matrix A[k] may be computed using a singular-value decomposition (SVD) well-known in the art:

$$A[k] = USV^T;$$ (Equation 2)

wherein U and V are both square unitary matrices, and S contains the singular values of A[k]. One of ordinary skill in the art will appreciate that a variety of software tools are available to calculate the singular values, or approximate singular values, of a given matrix, for the purpose of deriving the matrix S. Such software tools, include, e.g., the publicly available software packages LAPACK or EISPACK.

At step 350, the condition number C[k] is further refined by conversion into a "data condition number" DCN[k]. In an exemplary embodiment, DCN[k] may be computed as:

$$DCN[k] = 1 + \frac{(C[k]-1)}{N}. \quad \text{(Equation 3)}$$

The conversion from a condition number into a data condition number may be done to compensate for an expected quasi-linear increase in the condition number due to the number of channels N. Following the conversion, the data condition number may generally be processed independently of the number of channels. One of ordinary skill in the art will appreciate that alternative techniques for accounting for the number of channels may be employed. For example, the condition number need not be converted to a data condition number, and the thresholds used to determine the presence of anomalies may instead be adjusted by the number of channels. Such alternative exemplary embodiments are also contemplated to be within the scope of the present disclosure.

One of ordinary skill in the art will further appreciate that, in alternative exemplary embodiments, either the condition number C[k] or thresholds used may be alternatively, or further, normalized with respect to any source of variation in C[k] that is not of interest, i.e., not indicative of an anomaly. For example, variables such as the window size, signal measurement bandwidth, electrode montage, etc., may also be accounted for in converting the condition number C[k] to the data condition number DCN[k], and/or choosing the thresholds against which the DCN[k] is compared. Such additional coefficients and parameters may be calibrated empirically, and one of ordinary skill in the art may readily modify Equation 3 accordingly to account for such coefficients and parameters.

According to the present disclosure, the magnitude of the data condition number DCN[k] may serve as an indicator of whether a time window k of a multi-channel signal contains anomalies. For example, the DCN[k] may range from a value of 1, indicative of "healthy" data that is lacking in anomalies, to an arbitrarily large value ∞, indicative of "ill" data corresponding, e.g., to complete flatlining over the time window of interest. Evaluating the magnitude of each DCN[k] may provide an indication of whether a signal anomaly is present in the corresponding time window k.

In alternative exemplary embodiments (not shown), the DCN may be computed for a subset of the total number of signal sensors by constructing the matrix A[k] using such subset of signals, and employing the number of signals in the subset for the variable N. For example, instead of employing all N channels to construct the matrix A[k], only the signals from a subset N−1 of the channels may be used. This may be advantageous when, e.g., one of the signal sensors is known to be faulty. Such exemplary embodiments are contemplated to be within the scope of the present disclosure.

In alternative exemplary embodiments, the DCN may be computed from a subset N−1 of the channels to account for the effect of average montages, circular bipolar montages, or any other electrode montages, wherein one channel is known a priori to be a linear combination of all remaining channels, and therefore the matrix A[k] is rank-deficient.

One of ordinary skill in the art will appreciate that in light of the present disclosure, various alternative anomaly metrics to the condition number for detecting the presence of anomalies may be derived, based on, e.g., determining the independence or correlation between two or more of the channels. These alternative metrics may be derived based on the assumption that healthy data, especially in neurological multi-channel signals, is associated with independence among the channels, while data containing anomalies is associated with a lack of independence among the channels.

For example, for a square matrix A[k], a generalized condition number C'[k] may be derived as:

$$C'[k] = \text{Norm}(A[k]) \cdot \text{Norm}(A^{-1}[k]); \quad \text{(Equation 4)}$$

wherein Norm(·) denotes a norm of the matrix in parentheses, and $A^{-}[k]$ is the inverse of the square matrix A[k]. For example, norms such as the L1-norm and L-infinity norm are well-known in the art, and may be applied to compute an anomaly metric associated with a matrix A[k] in the following manner. One of ordinary skill in the art will appreciate that the L1-norm may be defined as the maximum of the column sums of A[k], and the L-infinity norm may be defined as the maximum of the row sums.

As the computation of the generalized condition number C'[k] and other types of condition numbers may require that the matrix A[k] be, e.g., a square matrix, or have other pre-specified dimensions, the data from the multi-channel signals may be suitably modified to ensure that the matrix A[k] takes on the proper form. For example, to ensure that the matrix A[k] is a square matrix, the size of the time window may be chosen such that the number of discrete time samples for each channel is equal to the total number of channels. Alternatively, the discrete time samples over a given time window may be sub-sampled at regular intervals to arrive at a square matrix A[k]. Such exemplary embodiments are contemplated to be within the scope of the present disclosure.

Figure 4A:
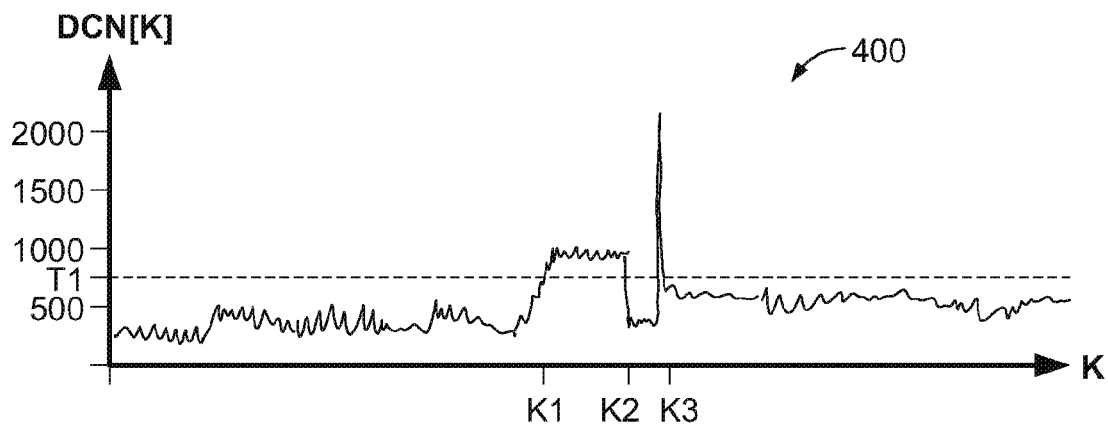
FIG. 4A illustrates a data condition number (DCN) time series obtained from a sample multi-channel signal using the steps of FIG. 3A and thresholding for event detection.
Figure 4A:
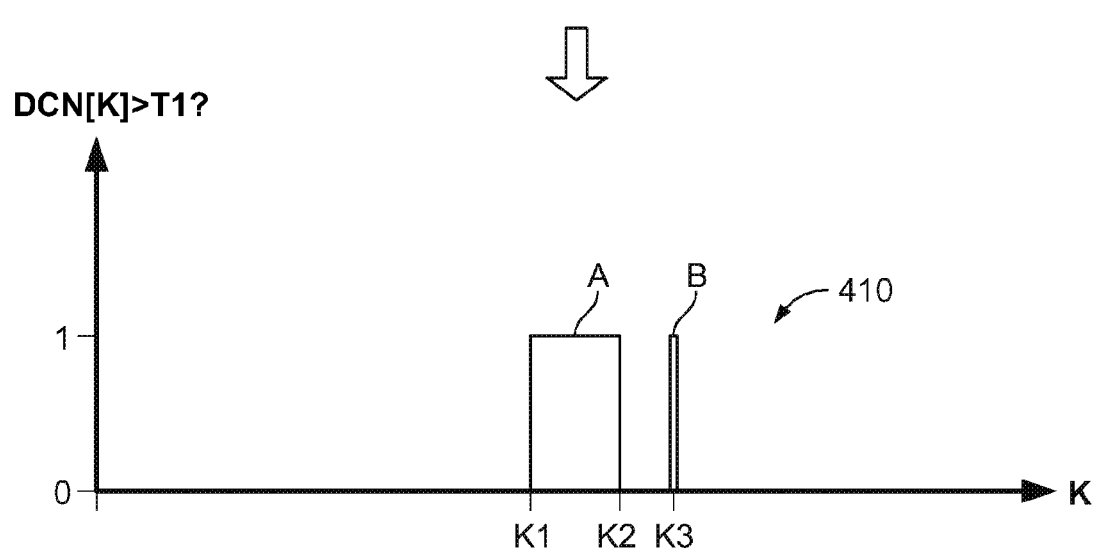

FIG. 4A illustrates a data condition number time series 400 obtained from a sample multi-channel signal using the steps of FIG. 3A and thresholding for event detection. In FIG. 4A, the horizontal axis depicts the time window index k, while the vertical axis depicts the value of DCN[k] corresponding to k. Note the absolute values of DCN[k] shown in FIG. 4A and discussed below are given for illustration only, and are not meant to restrict the techniques of the present disclosure to any particular values of DCN[k] shown. In particular, the absolute values of DCN[k] may depend on various parameters of the application.

In FIG. 4A, DCN[k] is shown to take on values generally less than 500 prior to time window k=K1. Between k=K1 and k=K2, DCN[k] is approximately 1000, while at time k=K2, DCN[k] is greater than 2000. In an exemplary embodiment, one or more predetermined thresholds may be chosen to identify the presence of anomalies in the multi-channel signal. For example, in FIG. 4A, the DCN[k] may be compared to a single threshold T1, and values of DCN[k] that are greater than the threshold T1 may indicate the presence of an "event" in the corresponding time window k. In an exemplary embodiment, the presence of an event may be taken to indicate the presence of an anomaly.

Further shown in FIG. 4A is an anomaly plot 410 generated from the time series 400 by comparison with threshold T1. Note anomaly plot 410 identifies the presence of two events A and B, possibly corresponding to two anomalies.

In alternative exemplary embodiments, two or more thresholds may be chosen for more precise categorization of the DCN. For example, in an exemplary embodiment, two thresholds T1 and T2 may be chosen, wherein T1<T2. In this exemplary embodiment, if the DCN is less than T1, then a lack of anomaly in the time window may be declared. If the DCN is greater than T2, then an anomaly can be automatically declared. If the DCN is between T1 and T2, then further processing, such as manual inspection of the multi-channel signal, may be performed to determine whether an anomaly is actually present. In an exemplary embodiment, patient-specific thresholds may be chosen that are customized to an individual patient whose neurological or other biological state is being monitored by the multiple sensors. Thresholds may be set differently for different patients, to account for the unique characteristics of each patient's bio-signals.

Figure 4B:
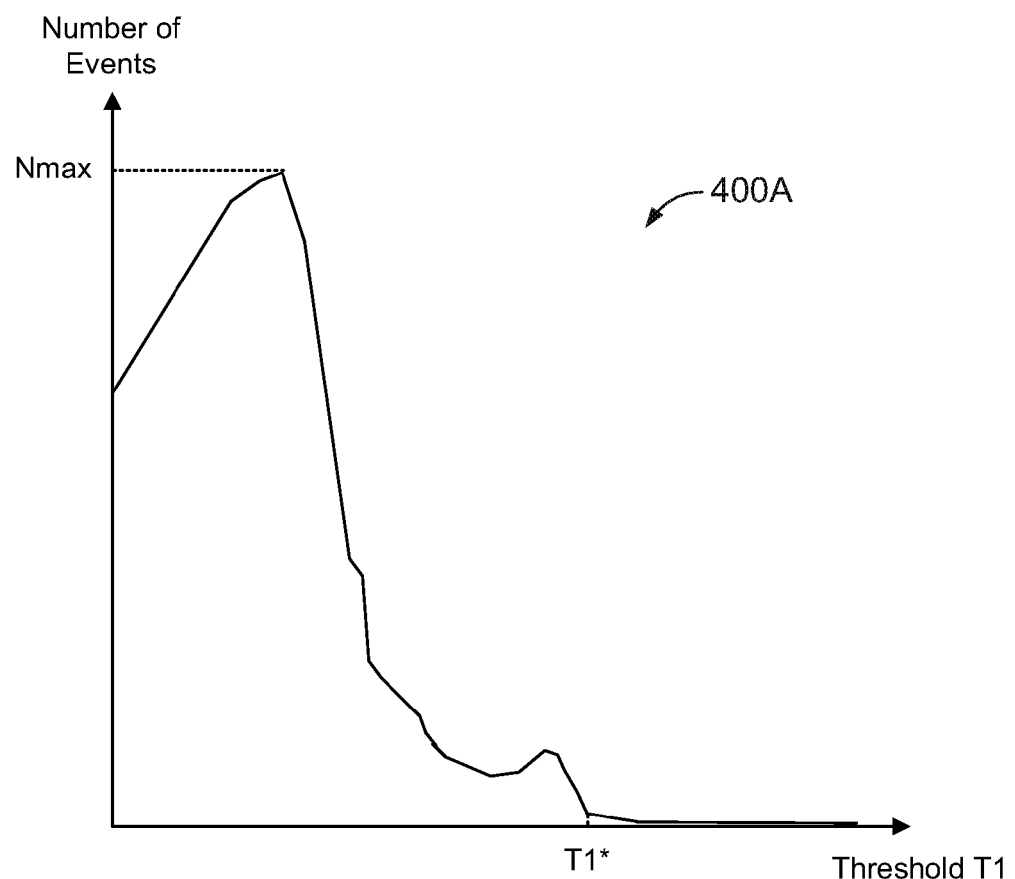
FIG. 4B illustrates a plot used in a procedure by which specific thresholds may be automatically chosen for any patient or group of patients.

According to an aspect of the present disclosure, specific thresholds may be automatically chosen for any patient or group of patients using a procedure as described with reference to the plot 400A shown in FIG. 4B. In FIG. 4B, the horizontal axis shows a candidate threshold T1, while the vertical axis tallies a number of events detected for the corresponding candidate threshold. Based on the plot 400A, an optimum threshold T1* may be chosen to, e.g., maximize the probability of detecting an anomalous event while minimizing the probability of "false" positives. In an exemplary embodiment, as shown in FIG. 4B, such an optimum threshold T1* may be chosen as, e.g., an inflection point of the plot 400A having the largest abscissa from amongst all inflection points, wherein an inflection is defined as a point where the curvature changes sign, e.g., from facing down to facing up. Alternatively, if such an inflection point does not exist (e.g., in exponential decay), the threshold T1* may be chosen as the minimum abscissa where the plot 400A drops to between 1% and 2% of its maximum value Nmax.

Figure 4C:
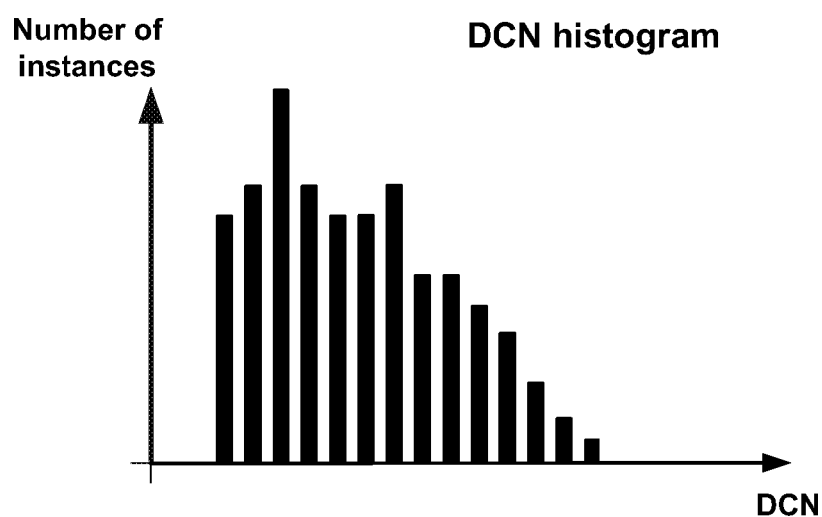
FIGS. 4C and 4D illustrate an alternative exemplary embodiment of a technique for choosing an optimum threshold T1*.
Figure 4D:
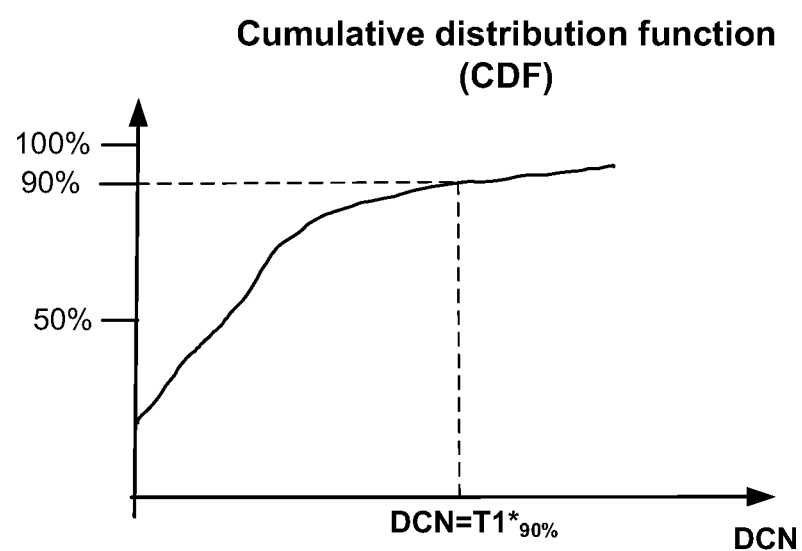

FIGS. 4C and 4D illustrate an alternative exemplary embodiment of a technique for choosing an optimum threshold T1*. FIG. 4C illustrates an exemplary histogram of DCN (horizontal axis), with the vertical axis showing the number of instances of the corresponding DCN in an arbitrary multi-channel signal (not shown). From the histogram of FIG. 4C, one of ordinary skill in the art may readily derive a corresponding cumulative distribution function (CDF), as shown in FIG. 4D, which indicates what percentage of events correspond to DCN's equal to or less than the shown DCN. One of ordinary skill in the art will appreciate that by selecting an appropriate percentage (e.g., 90% as illustrated in FIG. 4D), a corresponding threshold DCN of T1*, such as T1*$_{90\%}$ in FIG. 4D, may be automatically determined using the functional mapping provided by the CDF. One of ordinary skill in the art will further appreciate that in an exemplary embodiment, a computer may be programmed to perform such threshold selection, such that the choice of threshold may be made fully automatic without the need for manual intervention.

While certain exemplary techniques for automatically a choosing a suitable threshold T1* have been disclosed hereinabove, one of ordinary skill in the art will appreciate that alternative techniques not explicitly described may be readily derived in light of the present disclosure. Such alternative exemplary embodiments are contemplated to be within the scope of the present disclosure.

In alternative exemplary embodiments, additional properties of the DCN may be analyzed to further aid in the detection of anomalies in the multi-channel signal. For example, the rate of change of the DCN over a predetermined interval of time may also be utilized to detect the presence of an anomaly. Such modifications to the DCN and others not explicitly described will be clear to one of ordinary skill in the art, and are contemplated to be within the scope of the present disclosure.

Figure 5:
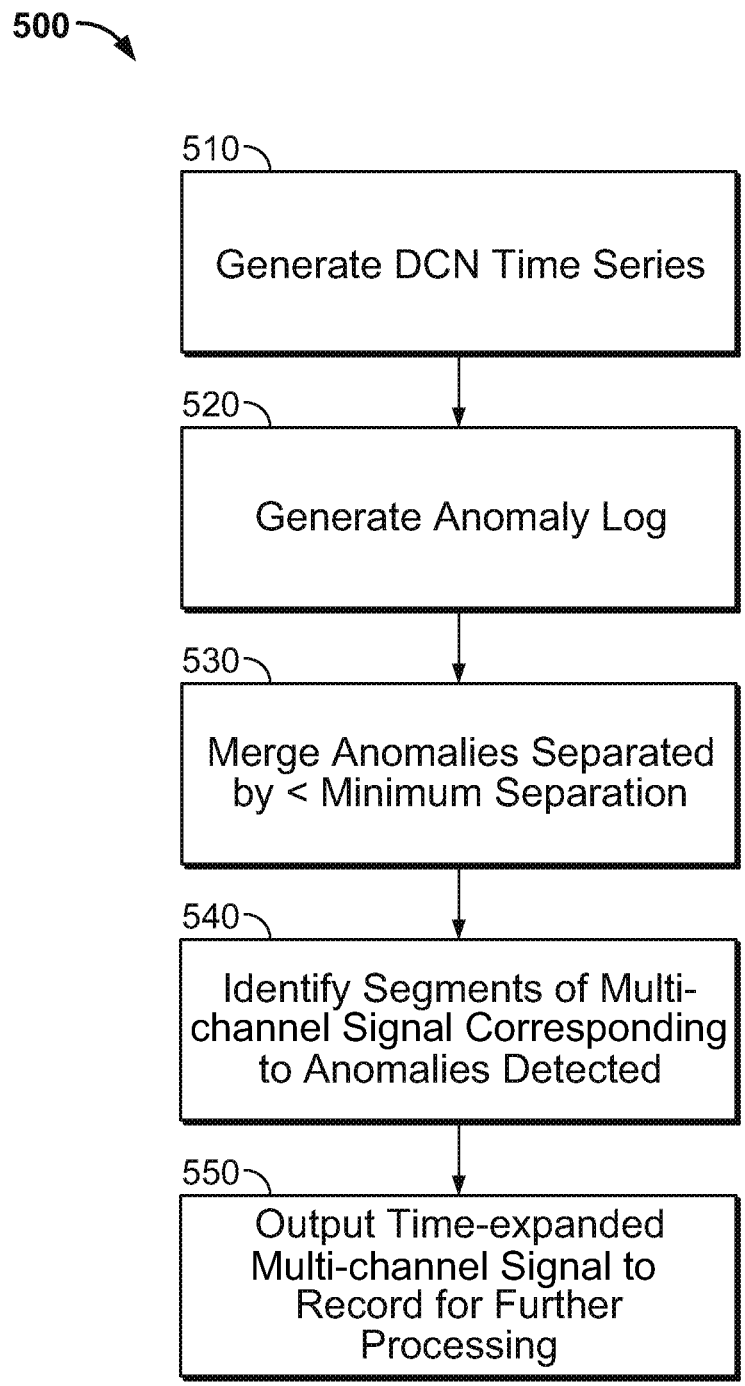
FIG. 5 depicts an exemplary method according to the present disclosure for taking action in response to the detection of an anomaly.

FIG. 5 depicts an exemplary method according to the present disclosure for taking action in response to the detection of an anomaly.

At step 510, a DCN time series such as 400 in FIG. 4A is generated from a multi-channel signal. In an exemplary embodiment, such a time series may be generated according to the method 300 depicted in FIG. 3A. However, one of ordinary skill in the art will appreciate that alternative methods may be employed to generate a suitable time series in light of the present disclosure.

At step 520, an anomaly log is generated based on the DCN time series. Such an anomaly log may identify, e.g., time window indices k in the DCN time series corresponding to detected anomalies. For example, in the exemplary embodiment wherein DCN[k] is compared to a single threshold T1 to determine the presence of an anomaly, the anomaly log may record all time window indices k wherein DCN[k] is larger than T1. As such, the anomaly log may effectively capture the relevant information from the anomaly plot 410.

One of ordinary skill in the art will appreciate that the information in an anomaly log may be recorded in several ways. For example, each line in the anomaly log may record the time index k associated with the beginning of a detected anomaly, and the corresponding time duration of the detected anomaly. Alternatively, the start and stop time indices associated with each detected anomaly may be recorded. Such exemplary embodiments are contemplated to be within the scope of the present disclosure.

At step 530, the complexity of the anomaly log may be reduced by merging separate anomalies that are separated by less than a minimum time separation. For example, assume two anomalies each of duration 10 are found in an anomaly log starting at time windows k=1 and k=12, i.e., the two anomalies are separated by a time duration of $\Delta k=1$. If a minimum time separation is defined as $\Delta k_{min}=5$, then the two anomalies may be merged to form a single anomaly, which can be recorded in a simplified anomaly log as a single merged anomaly of duration $\Delta k=21$ starting at k=1.

By performing the merging as described at step 530, the number of recorded anomalies and the size of the resulting anomaly log may be reduced to facilitate subsequent processing.

At step 540, the segments of the original multi-channel signal corresponding to the detected anomalies are identified.

At step 550, the identified segments of the multi-channel signal may be stored in an output record for post-processing. For example, the output record may be a computer file stored in a storage medium such as a computer hard drive, or it may be a paper print-out. In an exemplary embodiment, the identified segments output to the file may be expanded beyond those strictly associated with the anomalies. For example, fixed time segments of the multi-channel signal both immediately prior to and immediately subsequent to each identified data anomaly may also be output for each identified segment corresponding to an anomaly. The additional segments may further aid in the post-processing of the anomalies in the multi-channel signal, as further described hereinbelow.

In an exemplary embodiment (not shown), the output record generated by the method 500 may be manually reviewed, or "scrubbed," by a human technician to verify the presence of anomalies in the identified multi-channel signal segments. If the identified segment is verified to contain an anomaly, the segment may be, e.g., omitted from further post-processing, or other measures may be taken.

Figure 6:
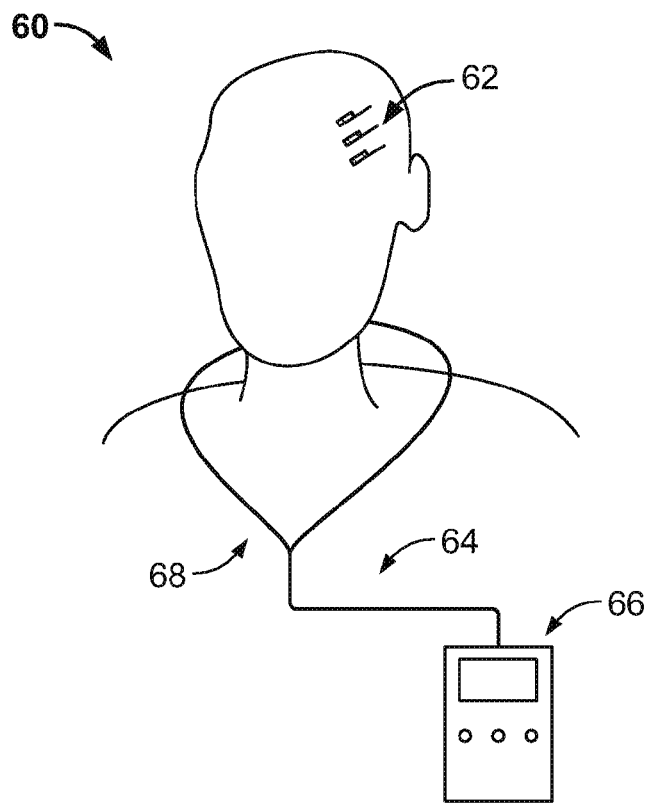
FIG. 6 depicts an alternative exemplary embodiment of the present disclosure, wherein the techniques disclosed hereinabove are applied in the context of a real-time patient monitoring and neurological event detection system.

FIG. 6 depicts an alternative exemplary embodiment of the present disclosure, wherein the techniques disclosed hereinabove are applied in the context of a real-time patient monitoring and neurological event detection system 60. For a more detailed description of the system in FIG. 6, see, e.g., "Minimally Invasive Monitoring Methods," U.S. patent application Ser. No. 11/766,751, filed Jun. 21, 2007, published as U.S. Patent Publication No. 2008/0027347A1 and assigned to the assignee of the present application, the contents of which are hereby incorporated by reference in their entirety. Note that FIG. 6 is provided for illustrative purposes only, and is not meant to limit the scope of the present disclosure in any way.

In FIG. 6, system 60 includes one or more implantable sensors or devices 62 that are configured to sample electrical activity from the patient's brain (e.g., EEG signals). The implantable devices may be active (with internal power source), passive (no internal power source), or semi-passive (internal power source to power components, but not to transmit data signal). The implantable devices 62 may be implanted anywhere in the patient. In an exemplary embodiment, one or more of the devices 62 may be implanted adjacent to a previously identified epileptic focus or a portion of the brain where the focus is believed to be located. Alternatively, the devices 62 themselves may be used to help determine the location of an epileptic focus In one aspect, the neural signals of the patient are sampled substantially continuously with the electrodes coupled to the electronic components of the implanted leadless device. A wireless signal is transmitted that is encoded with data that is indicative of the sampled neural signal from the implanted device to an external device. The wireless signal that is encoded with data that is indicative of the sampled neural signal is derived from the wireless signal received from the external device. The wireless signal can be any type of wireless signal—radiofrequency signal, magnetic signal, optical signal, acoustic signal, infrared signal, or the like.

The physician may implant any desired number of devices in the patient. As noted above, in addition to monitoring brain signals, one or more additional implanted devices 62 may be implanted to measure other physiological signals from the patient.

Implantable devices 62 may be configured to substantially continuously sample the brain activity of the groups of neurons in the immediate vicinity of the implanted device. The implantable devices 62 may be interrogated and powered by a signal from an external device 64 to facilitate the substantially continuous sampling of the brain activity signals. Sampling of the brain activity may be carried out at a rate above about 200 Hz, and preferably between about 200 Hz and about 1000 Hz, and most preferably at about 400 Hz, but it could be higher or lower, depending on the specific condition being monitored, the patient, and other factors. Each sample of the patient's brain activity may contain between about 8 bits per sample and about 32 bits per sample, and preferably between about 12 bits per sample and about 16 bits per sample.

In alternative embodiments, it may be desirable to have the implantable devices sample the brain activity of the patient on a non-continuous basis. In such embodiments, the implantable devices 62 may be configured to sample the brain activity signals periodically (e.g., once every 10 seconds) or aperiodically.

Implantable devices 16 may comprise a separate memory module for storing the recorded brain activity signals, a unique identification code for the device, algorithms, other programming, or the like.

A patient instrumented with the implanted devices 62 may carry a data collection device 64 that is external to the patient's body. The external device 64 would receive and store the signals from the implanted devices 62 with the encoded EEG data (or other physiological signals). The signals received from the plurality of implanted devices 62 may be represented as a multi-channel signal, and may be preprocessed according to the techniques of the present disclosure. The external device 64 is typically of a size so as to be portable and carried by the patient in a pocket or bag that is maintained in close proximity to the patient. In alternative embodiments, the device may be configured to be used in a hospital setting and placed alongside a patient's bed. Communication between the data collection device 64 and the implantable device 62 may take place through wireless communication. The wireless communication link between implantable device 62 and external device 64 may provide a communication link for transmitting data and/or power. External device 64 may include a control module 66 that communicates with the implanted device through an antenna 68. In the illustrated embodiment, antenna 68 is in the form of a necklace that is in communication range with the implantable devices 62.

Transmission of data and power between implantable device 62 and external device 64 may be carried out through a radiofrequency link, infrared link, magnetic induction, electromagnetic link, Bluetooth® link, Zigbee link, sonic link, optical link, other types of wireless links, or combinations thereof.

In an exemplary embodiment, the external device 64 may include software to pre-process the data according to the present disclosure and analyze the data in substantially real-time. For example, the received RF signal with the sampled EEG may be analyzed for the presence of anomalies according to the present disclosure, and further by EEG analysis algorithms to estimate the patient's brain state which is typically indicative of the patient's propensity for a neurological event. The neurological event may be a seizure, migraine headache, episode of depression, tremor, or the like. The estimation of the patient's brain state may cause generation of an output. The output may be in the form of a control signal to activate a therapeutic device (e.g., implanted in the patient, such as a vagus nerve stimulator, deep brain or cortical stimulator, implanted drug pump, etc.).

In an exemplary embodiment, the output may be used to activate a user interface on the external device to produce an output communication to the patient. For example, the external device may be used to provide a substantially continuous output or periodic output communication to the patient that indicates their brain state and/or propensity for the neurological event. Such a communication could allow the patient to manually initiate self-therapy (e.g., wave wand over implanted vagus nerve stimulator, cortical, or deep brain stimulator, take a fast acting anti-epileptic drug, etc.).

In an alternative exemplary embodiment, the external device 64 may further communicate with an auxiliary server (not shown) having more extensive computational and storage resources than can be supported in the form factor of the external device 64. In such an exemplary embodiment, the anomaly pre-processing and EEG analysis algorithms may be performed by an auxiliary server, or the computations of the external device 64 may be otherwise facilitated by the computational resources of the auxiliary server.

Figure 7:
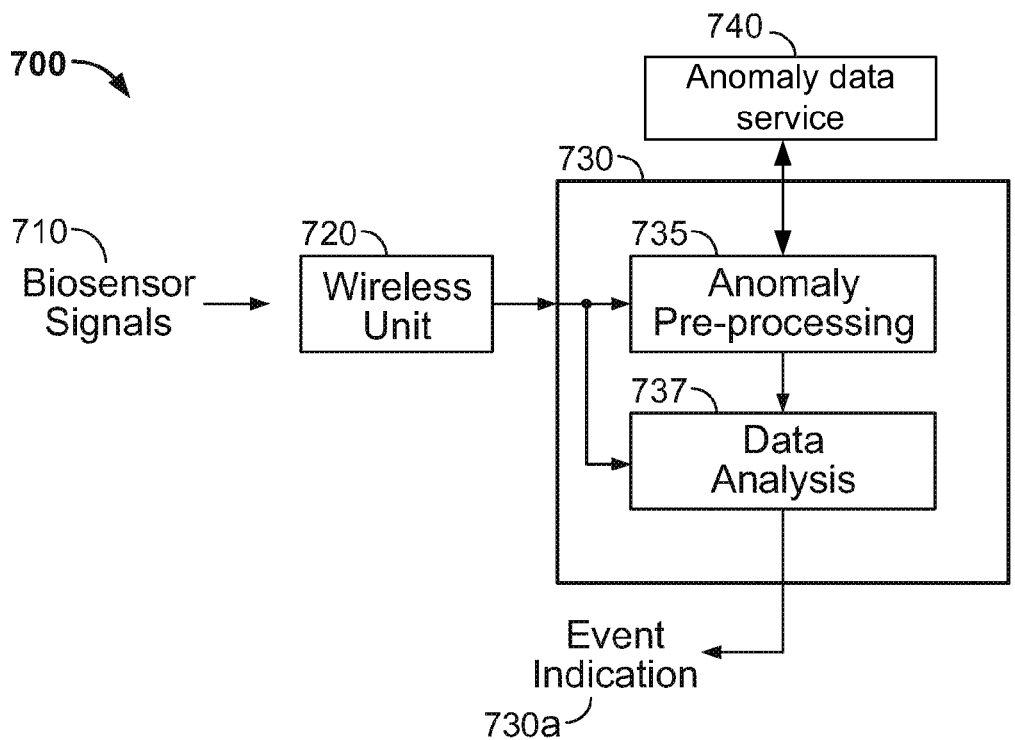
FIG. 7 depicts a generalized block diagram of the real-time analysis system featuring an anomaly pre-processing block according to the present disclosure.

FIG. 7 depicts a generalized block diagram 700 of the real-time analysis system 60 featuring an anomaly pre-processing block 735 according to the present disclosure. One of ordinary skill in the art will appreciate that the block diagram 700 need not be limited to the exemplary system 60 shown in FIG. 6, but may also be broadly applicable to other types of multi-channel sensing and processing systems.

In FIG. 7, biosensor signals 710 form a multi-channel signal that is provided over a wireless link to wireless unit 720. Wireless unit 720 communicates the multi-channel signal to a processing module 730 that may be resident either on the wireless unit 720 itself, or separately from the wireless unit 720, as described with reference to FIG. 6. When residing separately from the wireless unit 720, the processing module 730 may be configured to run algorithms, perform computations, or perform anomaly checking that may be too complex or intensive for a low-power wireless unit 720 to implement. Such anomaly checking may correspond to the "self-checking" techniques as further described hereinbelow with reference to FIG. 8.

Processing module 730 includes a pre-processing block 735 that identifies and processes anomalies in the multi-channel signal. The output of pre-processing block 735 is provided to a data analysis block 737, which may output an event indicator 730a. The output event indicator 730a may correspond to the output of the estimation of the patient's brain state as described with reference to FIG. 6.

In the exemplary embodiment shown, the pre-processing block 735 communicates with an anomaly data service 740. The anomaly data service 740 may reside remotely from the processing module 730, and may provide the pre-processing block 735 with dynamically adjusted thresholds and/or other parameters to aid the pre-processing block 735 in identifying anomalies in the multi-channel signal. For example, the anomaly data service 740 may analyze anomalies from a plurality of multi-channel signals sampled over a population of seizure detection systems, seizure prediction systems, and/or seizure counter-prediction systems. The anomaly data service 740 may periodically derive preferred DCN comparison thresholds for use in the individual real-time analysis system 700. In an exemplary embodiment, the real-time analysis system 700 may also upload data samples to the anomaly data service 740 to aid the anomaly data service 740 in deriving preferred thresholds.

In an exemplary embodiment, the anomaly data service 740 may communicate with the processing module 730 wirelessly. Alternatively, the anomaly data service 740 may communicate with the processing module 730 over a wired connection. In yet another exemplary embodiment, the anomaly data service 740 may be omitted altogether, and the pre-processing block 735 may simply rely on pre-programmed threshold values. Such exemplary embodiments are contemplated to be within the scope of the present disclosure.

Figure 8:
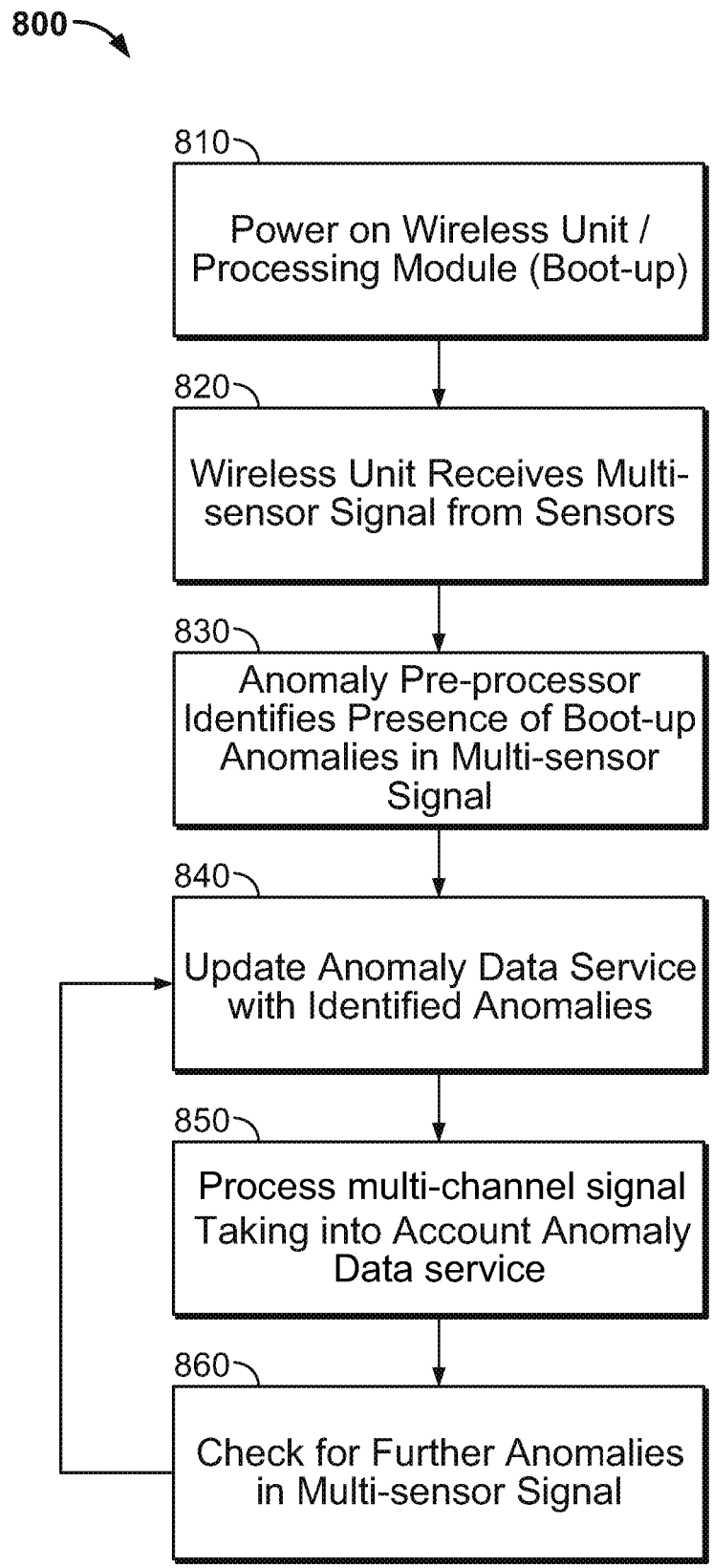
FIG. 8 depicts an exemplary method according to the present disclosure that may be implemented, e.g., using the system shown in FIG. 7.

FIG. 8 depicts an exemplary method 800 according to the present disclosure that may be implemented, e.g., using the system 700. Note the exemplary method is shown for illustrative purposes only, and is not meant to limit the scope of the present disclosure to any particular method disclosed.

At step 810, the wireless unit 720 and processing module 730 are powered on.

At step 820, the wireless unit 720 receives the multi-channel signal from, e.g., a plurality of biosensors such as implanted devices 62 in FIG. 6.

At step 830, anomaly pre-processor 735 in processing module 730 identifies the presence of boot-up anomalies in the multi-channel signal received at step 820. This step may also be termed "self-checking," or "self-test diagnostics."

In an exemplary embodiment, "boot-up" anomalies may be any anomalies identified in the multi-channel signal during an initial boot-up phase. The boot-up phase may correspond to a time when software in the processing module 730 is initialized, and/or other parameters of the system 700 are initially configured. For example, the boot-up phase may last for a fixed amount of time after the wireless unit 720 and processing module 730 are powered on at step 800.

In an exemplary embodiment, the identification of anomalies in the multi-channel signal may be performed using the DCN computation techniques earlier described herein with reference to FIG. 3A. However, anomaly identification need not be performed using DCN computation. Anomaly identification in the method 800 may generally be performed using any suitable anomaly detection metric or metrics derivable by one of ordinary skill in the art in light of the present disclosure. Such alternative exemplary embodiments are contemplated to be within the scope of the present disclosure.

At step 840, an anomaly central data service may be continuously updated during operation of the method 800 with appropriate thresholds and/or algorithms for detecting the presence of anomalies in the multi-channel signal. In an exemplary embodiment, the anomaly data service may update a series of thresholds T1, T2, etc., against which the data condition number (DCN) is compared to detect the presence of anomalies in the multi-channel signal. The anomaly data service may vary the value of such thresholds over time, based on, e.g., offline analysis of anomalies and associated anomaly metrics as computed over an entire population of multi-channel signals.

At step 850, operation of the system 700 proceeds with the processing module 730 processing the multi-channel signal, taking into account the information in the anomaly data service.

At step 860, the anomaly processor 735 checks for anomalies in the multi-channel signal during normal operation of the system 700. The checking at step 860 may be termed "adaptive" anomaly identification and processing, as contrasted with the "boot-up" anomaly identification and processing described with reference to step 830. Information about anomalies identified during step 860 may be used to update the anomaly data service, as illustrated by the return arrow from step 860 to step 840, and as earlier described with reference to block 740 hereinabove. The steps 840, 850, 860 may be continuously repeated during normal operation of the system 700. An advantage of the adaptive anomaly identification and processing techniques described herein is that they may be varied over an extended temporal context used to monitor the multi-channel signal, as compared to the one-time self-checking diagnostics provided during a boot-up phase.

In an exemplary embodiment, entries from the anomaly data service may also be removed from the data service if anomaly processor 735 determines that such anomalies are no longer applicable. Such exemplary embodiments are contemplated to be within the scope of the present disclosure.

Figure 9A:
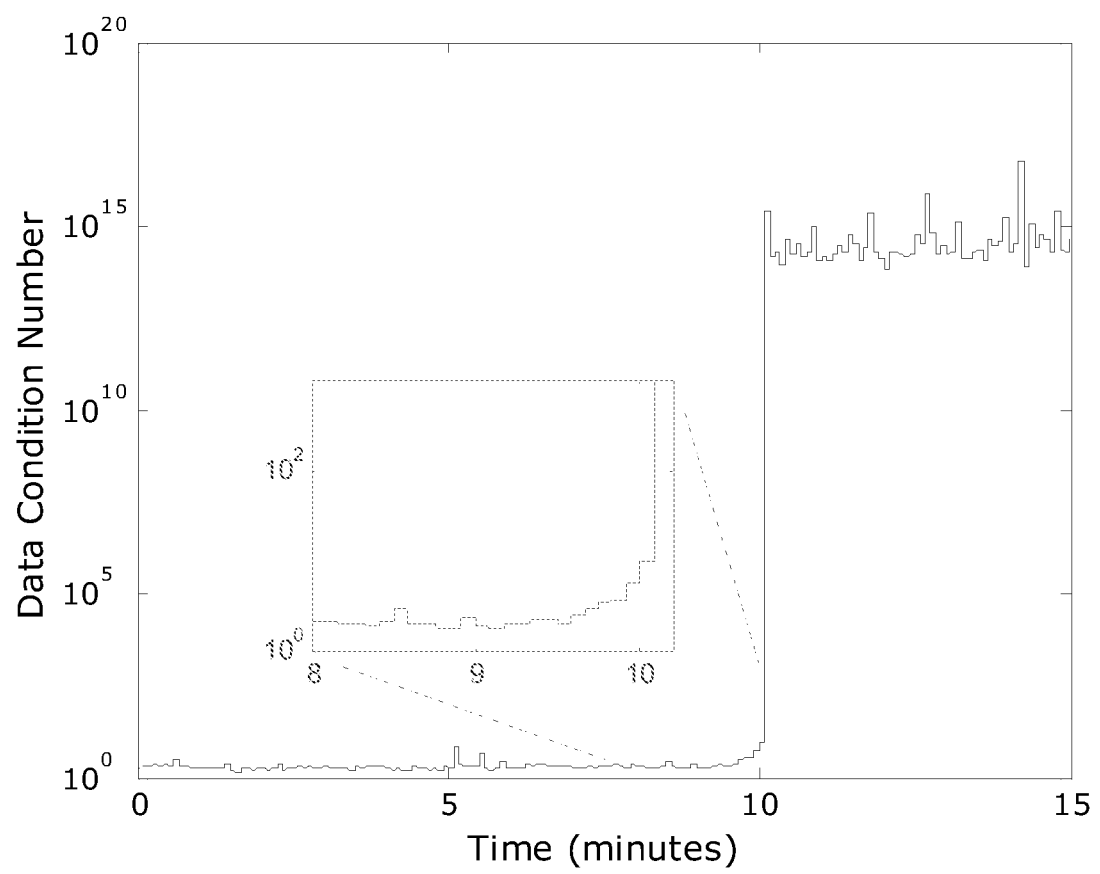
FIGS. 9A and 9B illustrate exemplary plots of data condition number (DCN) versus time, corresponding to certain specific operating scenarios.

FIG. 9A illustrates an exemplary plot of data condition number (DCN) versus time, corresponding to an operating scenario wherein two of the sensors used to generate a multi-channel signal are gradually electrically shorted together during the interval starting from Time=5 minutes to Time=10 minutes. The scenario shown may arise, e.g., when two adjacent connectors at a distal end of a lead assembly implanted in a patient are gradually shorted together, effectively forming a path for interconnect ionic migration.

As seen in FIG. 9A, the DCN increases to extremely high levels in response to the gradual electrical shorting, and takes on values as high as $10^{15}$ when two of the leads are eventually completely shorted together, and converging to their common average, after Time=10 minutes. This expected behavior of the DCN in response to a physical condition such as electrical shorting allows the DCN to be used as an effective detection metric for indicating when such conditions might arise in an actual scenario. For example, by detecting when the DCN exceeds a suitably high threshold, the error condition wherein there is electrode shortage may be flagged to an automated software module, or to a manual user. One of ordinary skill in the art will appreciate that alternative techniques may also be employed to detect such an error condition, e.g., pattern matching the observed DCN to expected behavior of the DCN in the presence of the error condition, such expected behavior being obtained through, e.g., prior simulation or historical data. Furthermore, through further processing, e.g., by computing and evaluating the DCN over specific subsets of channels of the multi-channel signal, the specific leads causing the electrical shortage problem may be specifically identified and dealt with.

Figure 9B:
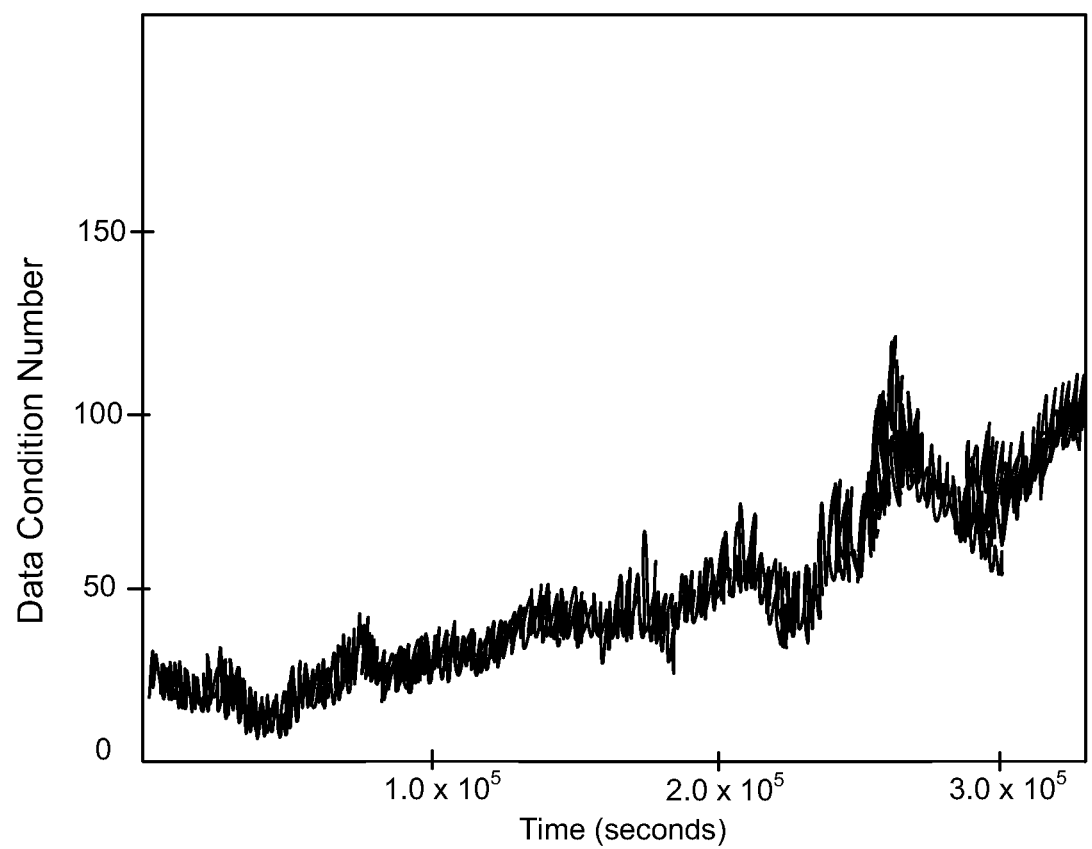

FIG. 9B illustrates an exemplary plot of data condition number (DCN) versus time, corresponding to an operating scenario wherein there is a gradual loss of contact of a reference electrode used to sample the multi-channel signal, over the span of about three days. As seen in FIG. 9B, there is a noticeable upward trend in the DCN over the time interval shown. In an exemplary embodiment, the presence of such an upward trend in the DCN may be used to detect the condition corresponding to gradual loss of contact of an electrode. Such a condition may then be flagged to an automated software module, or to a manual user. One of ordinary skill in the art will appreciate that various techniques may be employed to quantify any upward trend in the DCN. For example, a low-pass filter may be applied to the DCN time-series, and absolute increases in the DCN over a suitably long time period may be assessed and compared to some threshold. Alternatively, other pattern matching techniques may also be employed. Such alternative exemplary embodiments are contemplated to be within the scope of the present disclosure.

Figure 10A:
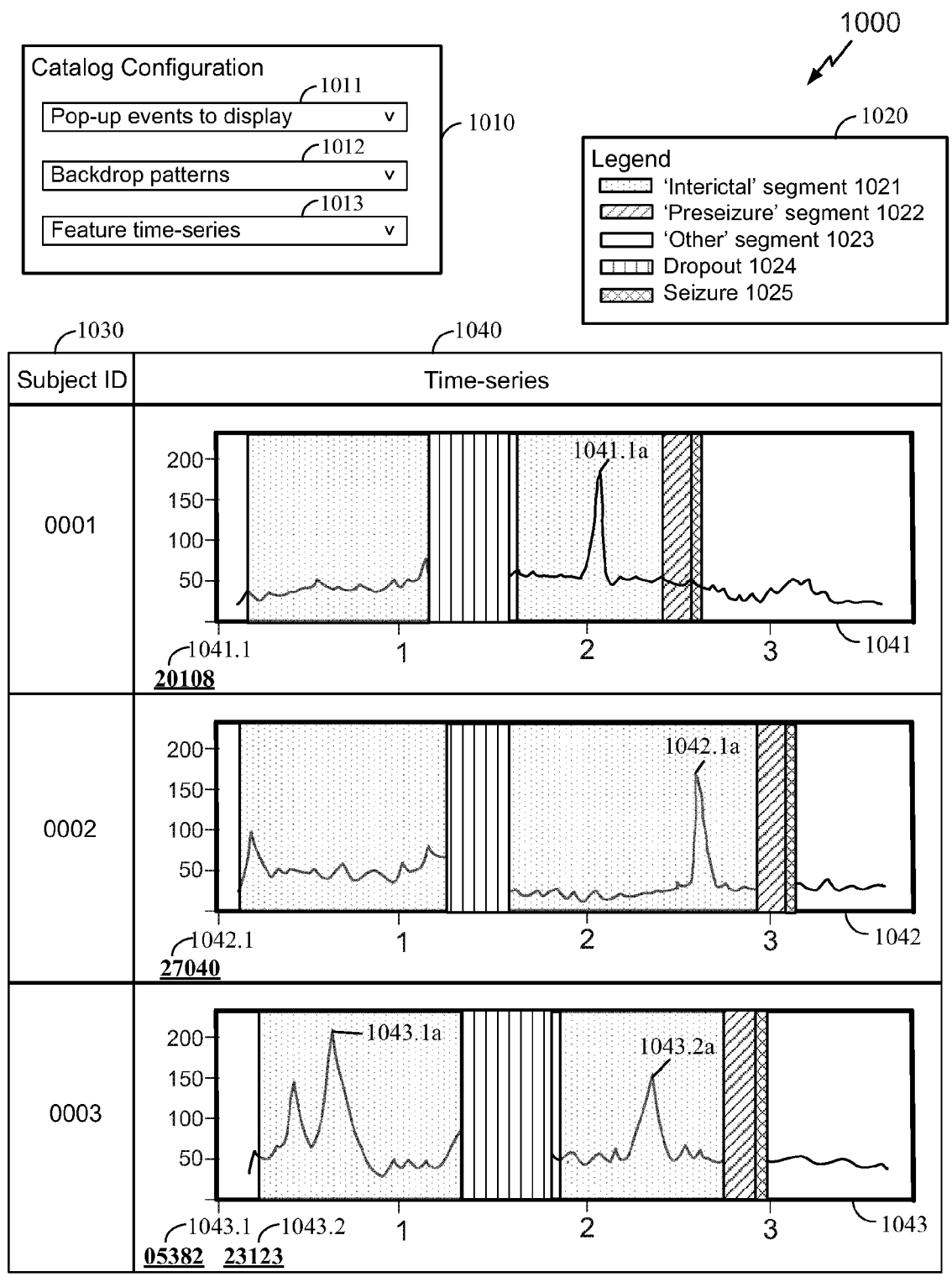
FIGS. 10A and 10B illustrate an exemplary embodiment of a graphical display interface for conveniently displaying information associated with the techniques of the present disclosure.

FIG. 10A illustrates an exemplary embodiment of a graphical display interface 1000 for simultaneously displaying various types of information associated with the techniques of the present disclosure. Note the exemplary embodiment of FIG. 10A is shown for illustrative purposes only, and is not meant to limit the scope of the present disclosure to any particular graphical display interface shown. One of ordinary skill in the art will appreciate that the graphical display interface 1000 may be a "screen shot," i.e., an instantaneous sample of the image on a computer screen displayed when a user (e.g., a technician) is using the disclosed graphical interface to analyze data. The graphical display may be generated by, e.g., computer software running on a general-purpose computer, and may be readily designed by one of ordinary skill in the art in light of the further description given hereinbelow. For example, in an exemplary embodiment, such computer software may be conveniently accessed via a Web browser.

In FIG. 10A, graphical display interface 1000 includes a graphical representation of a catalog configuration block 1010, a graphical representation of a legend 1020, and a series of time-series displays 1040. The time-series displays 1040 may include time series 1041, 1042, 1043, each associated with a corresponding subject identification number as denoted in the subject ID column 1030. In the exemplary embodiment shown, there are three subject ID's 0001, 0002, and 0003. One of ordinary skill in the art will appreciate that the techniques disclosed herein may readily be applied to display information associated with any number of subjects, per the requirements of the application.

The catalog configuration block 1010 includes a series of drop-down menus 1011, 1012, and 1013.

Drop-down menu 1012 allows the user to select a scheme for backdrop patterns used to highlight certain information contained in the time-series displays 1040. In an exemplary embodiment, the mapping between a type of information and a corresponding backdrop pattern used to highlight such information type may be as shown according to the legend 1020. The legend 1020 indicates backdrop patterns used to show an 'interictal' segment 1021, a 'preseizure' segment 1022 (e.g., a fixed preictal time interval), other segment 1023, dropout 1024 (e.g., lapsed or invalid data), and seizure event 1025. As shown in the time-series 1041, 1042, and 1043, the backdrop patterns identified in legend 1020 may be used to annotate the time-series displays 1040 with information in a concise and easily presented form for convenient analysis by a user of the graphical display interface 1000.

One of ordinary skill in the art will appreciate that various modifications to the backdrop pattern scheme shown are readily derivable in light of the present disclosure. For example, in a color graphical display interface (not shown), backdrop colors may be used in place of, or in addition to, the backdrop patterns shown. A color scheme may assign a distinct color to each of the following types of segments: "interictal" segments, "preseizure" segments, "other" segments, "dropouts" (e.g., lapsed or invalid data), and "seizure" events. Alternative exemplary embodiments may also include other types of information not explicitly shown in FIG. 10A. Such alternative exemplary embodiments are contemplated to be within the scope of the present disclosure.

Drop-down menu 1013 allows the user to select the quantity to be displayed on the vertical axes of the time-series displays 1040. For example, one selectable quantity may be a data condition number (DCN) as calculated for each subject according to the present disclosure, plotted versus time. Alternative types of quantities include, e.g., the channel-sum of line-lengths (sum of absolute deviations in time) or its spatiotemporal and normalized variants, which would be appropriate for large-scale temporal localization of seizures rather than EEG anomalies.

Figure 10B:
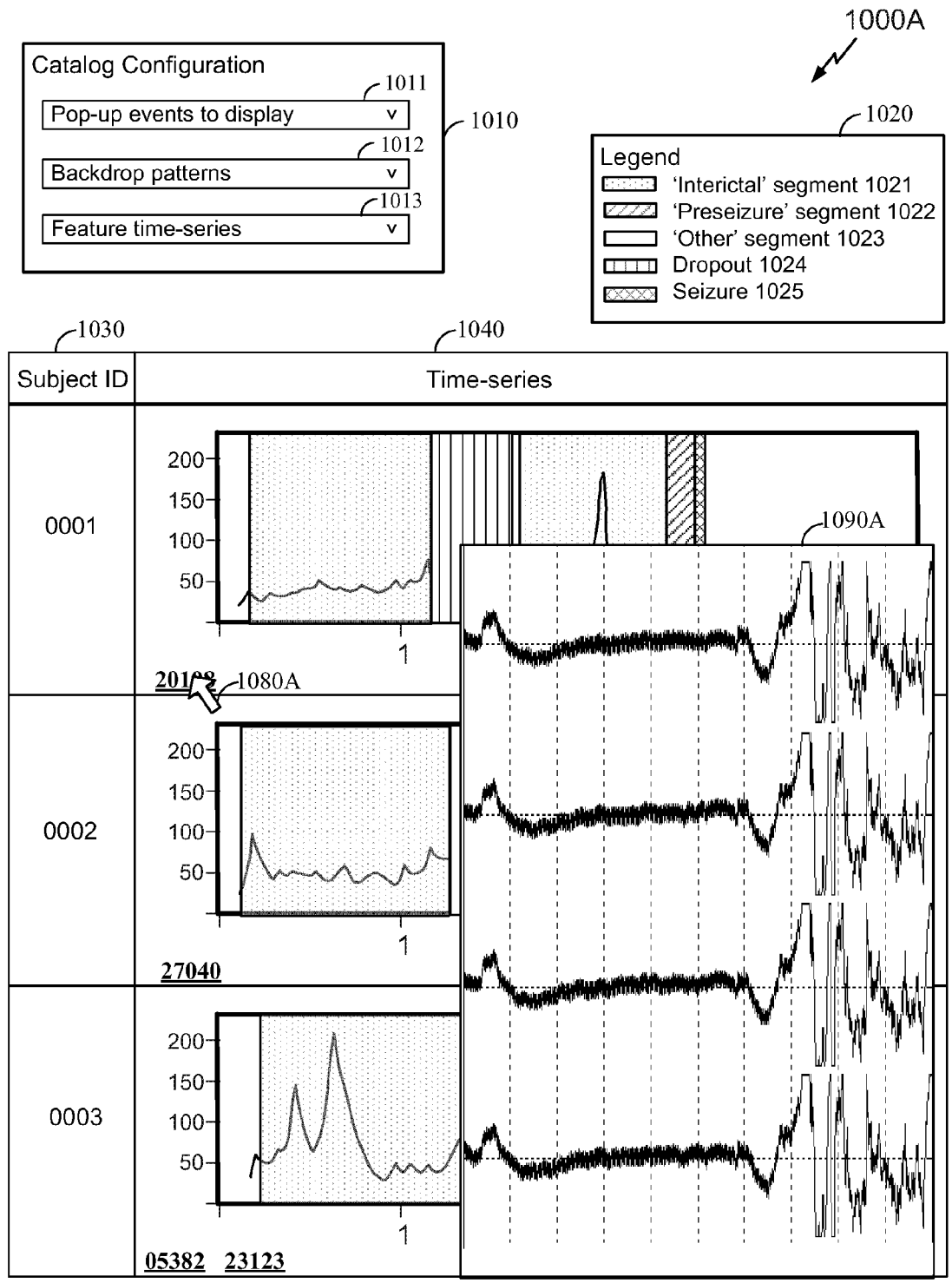

As further shown in FIG. 10A, time series 1041 is accompanied by a time event index 1041.1. In the exemplary embodiment shown, the time event index 1041.1 is shown in bold and underlined, and has a numerical value of 20108. The time event index 1041.1 may indicate a time index in the time series 1041 wherein the corresponding DCN value exceeds some pre-specified threshold. See, e.g., the portion of time series 1041 indicated by 1041.1a. As more clearly shown in FIG. 10B, by rolling a cursor 1080A over the time event index 1041.1, an auxiliary window 1090A may "pop up" in the same display. Alternatively, the time event index 1041.1 may be "hyperlinked," such that placing the cursor 1080A over the time event index 1041.1 and clicking the index 1041.1 causes the auxiliary window 1090A to simultaneously pop up.

The information content, or type of event, shown in the auxiliary window 1090A may be selected via the drop-down menu 1011. In the exemplary embodiment shown in FIG. 10B, the auxiliary window 1090A may show, e.g., the portion of the original multi-channel signal (such as EEG data) from which the DCN value corresponding to the time event index 1041.1 was derived. The auxiliary window 1090A advantageously allows the graphical interface user to visually inspect the portion of the multi-channel signal giving rise to the above-threshold DCN value alongside the DCN time-series, and manually determine whether the identified portion is in fact anomalous.

Other pop-up events to display may include context menus that direct the user to the raw EEG data where an anomaly can be further inspected in full detail.

As shown for indices 1043.1 and 1043.2 associated with time-series 1043, there may be multiple points in a time series wherein a DCN value exceeds a pre-specified threshold, and thus there may generally be multiple event indices associated with each time-series.

Based on the teachings described herein, it should be apparent that an aspect disclosed herein may be implemented independently of any other aspects and that two or more of these aspects may be combined in various ways. In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD/DVD-ROM or other optical disk storage, magnetic disk storage or other magnetic storage devices, solid-state flash cards or drives, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-Ray disc where disks usually reproduce data magnetically, while discs reproduce data optically with lasers. Combinations of the above should also be included within the scope of computer-readable media.

In this specification and in the claims, it will be understood that when an element is referred to as being "connected to" or "coupled to" another element, it can be directly connected or coupled to the other element or intervening elements may be present. In contrast, when an element is referred to as being "directly connected to" or "directly coupled to" another element, there are no intervening elements present.

A number of aspects and examples have been described. However, various modifications to these examples are possible, and the principles presented herein may be applied to other aspects as well. These and other aspects are within the scope of the following claims.

What is claimed is:

1. A method for displaying information to a user, the method comprising:
   accepting input from the user selecting a metric to be displayed, said selected metric being associated with a multi-channel signal derived from outputs of a plurality of sensors positioned to acquire physiological signals, wherein each channel of the multi-channel signal corresponds to a different one of the plurality of sensors;
   displaying with a processor and a computer graphical display interface at least one time-series plot of the selected metric associated with the multi-channel signal;
   using a backdrop pattern, indicating on the at least one time-series plot portions of the plot having at least one identified characteristic;
   for each of the at least one time-series plot displayed, displaying with the processor and the computer graphical display interface a time event index wherein the corresponding metric meets a predetermined condition, wherein the predetermined condition comprises the selected metric being greater than a predetermined threshold;
   accepting input from the user as to whether to display further information associated with the time event index; and
   displaying the further information associated with the time event index when the user so specifies.

2. The method of claim 1, the metric comprising a data condition number calculated for the multi-channel signal.

3. The method of claim 1, the at least one time-series plot comprising a plurality of time-series plots, each time-series plot associated with a subject ID.

4. The method of claim 1, the at least one identified characteristic including a portion of the time-series corresponding to a seizure segment.

5. The method of claim 1, the backdrop pattern comprising a color scheme, the color scheme representing "interictal" segments, "preseizure" segments, "other" segments, "dropouts," and "seizure" events.

6. The method of claim 1, the input from the user as to whether to display further information associated with the time event index comprising positioning of a cursor over the time event index.

7. The method of claim 1, further comprising:
   accepting input from the user indicating a color scheme for the backdrop pattern to be used.

8. The method of claim 1, the displaying the further information associated with the time event index comprising:
   displaying a pop-up plot of a portion of the multi-channel signal corresponding to the time event index.

9. The method of claim 8, the multi-channel signal comprising a multi-channel EEG signal.

10. A method for detecting anomalies in a multi-channel signal, the method comprising:
    sampling the multi-channel signal over a time window;
    computing with a processor an anomaly metric for the multi-channel signal over the time window; and
    identifying the presence of an anomaly based on the magnitude of the anomaly metric; the computing an anomaly metric comprising:
    computing a condition number of the multi-channel signal over the time window; and
    adjusting the condition number based on a parameter of the multi-channel signal to generate a data condition number (DCN); the multi-channel signal comprising a signal sampled from a plurality of electrodes positioned to acquire physiological signals from a body, the method further comprising:
    generating a DCN time series corresponding to a plurality of time windows;
    generating an anomaly log based on the DCN time series;
    merging anomalies in the anomaly log separated by less than a minimum separation to generate a modified anomaly log;
    identifying segments of the multi-channel signal corresponding to anomalies in the modified anomaly log; and
    outputting time-expanded versions of the identified segments to a record; the identifying the presence of an anomaly comprising matching the DCN time series to at least one known pattern of DCN time series corresponding to an anomalous condition.

11. A method for detecting anomalies in a multi-channel signal, the method comprising:

sampling the multi-channel signal over a time window;
computing with a processor an anomaly metric for the multi-channel signal over the time window; and
identifying the presence of an anomaly by comparing the magnitude of the anomaly metric to an optimum threshold; the computing an anomaly metric comprising:
computing a condition number of the multi-channel signal over the time window; and
adjusting the condition number based on a parameter of the multi-channel signal to generate a data condition number (DCN); the method further comprising:
generating a DCN time series corresponding to a plurality of time windows;
generating an event log based on the DCN time series, the generating an event log comprising identifying an event as a contiguous set of DCN values greater than a candidate threshold;
merging events in the event log separated by less than a minimum separation to generate a modified event log;
repeating the steps of generating a DCN time series, generating an event log, and merging events using a plurality of candidate thresholds;
generating a plot of number of events identified in a modified event log versus candidate threshold used;
attempting to identify at least one inflection point in the generated plot; and
setting the optimum threshold to be the candidate threshold corresponding to the inflection point with the largest abscissa in the plot.

12. The method of claim 11, further comprising, when the attempt to identify at least one inflection point is unsuccessful:
identifying a maximum number of events corresponding to a candidate threshold in the histogram; and
setting the optimum threshold to be a candidate threshold whose corresponding number of events is less than or equal to a fixed percentage of the maximum number of events.

* * * * *